United States Patent
Arbel et al.

(10) Patent No.: US 7,771,364 B2
(45) Date of Patent: Aug. 10, 2010

(54) METHOD AND SYSTEM FOR CARDIOVASCULAR SYSTEM DIAGNOSIS

(75) Inventors: Ronen Arbel, Tel Aviv (IL); Yoram Tal, Tel Aviv (IL); Michael Ortenberg, Kfar Yona (IL)

(73) Assignee: Spirocor Ltd., Yoqneam (IL)

( * ) Notice: Subject to any disclaimer, the term of this patent is extended or adjusted under 35 U.S.C. 154(b) by 21 days.

(21) Appl. No.: 12/194,139

(22) Filed: Aug. 19, 2008

(65) Prior Publication Data

US 2009/0076399 A1 Mar. 19, 2009

Related U.S. Application Data

(63) Continuation-in-part of application No. 11/892,256, filed on Aug. 21, 2007, which is a continuation-in-part of application No. 11/489,721, filed on Jul. 20, 2006, which is a continuation-in-part of application No. PCT/IL2005/000095, filed on Jan. 27, 2005.

(60) Provisional application No. 60/539,117, filed on Jan. 27, 2004.

(51) Int. Cl.
*A61B 5/02* (2006.01)
*A61B 5/08* (2006.01)

(52) U.S. Cl. ............... 600/500; 600/484; 600/483; 600/485

(58) Field of Classification Search ............... 600/481, 600/483, 484, 500–503, 529, 300, 301
See application file for complete search history.

(56) References Cited

U.S. PATENT DOCUMENTS 4,832,038 A * 5/1989 Arai et al. ............... 600/483
4,896,675 A 1/1990 Ohsuga et al.
5,299,119 A 3/1994 Kraf et al.
5,623,933 A 4/1997 Amano et al.
6,216,032 B1 4/2001 Griffin et al.
6,299,582 B1 10/2001 Brockway et al.
6,319,205 B1 11/2001 Goor et al.
6,322,515 B1 11/2001 Goor et al.

(Continued)

FOREIGN PATENT DOCUMENTS

EP 0113200 11/1988

(Continued)

OTHER PUBLICATIONS

"Assessment of vasoactive agents and vascular ageing by the second derivative of photoplethysmograph waveform", 1998, Hypertension, 32:365-370.

(Continued)

*Primary Examiner*—Robert L Nasser
*Assistant Examiner*—Navin Natnithithadha
(74) *Attorney, Agent, or Firm*—Pearl Cohen Zedek Latzer, LLP

(57) ABSTRACT

The present invention is directed to a method and system for monitoring function and/or diagnosing dysfunction of the cardiovascular system of a human subject. The method comprise measuring pulse wave signals of the subject during rapid excitation of the cardiovascular system, analyzing the measured signals and computing indicators reflecting a response to said excitation. The cardiovascular excitation preferably comprise a controlled breathing protocol characterized by a predefined frequency of breaths (e.g., about 0.1 Hz).

13 Claims, 19 Drawing Sheets

U.S. PATENT DOCUMENTS

| | | |
|---|---|---|
| 6,330,469 B1 | 12/2001 | Griffin et al. |
| 6,527,729 B1 * | 3/2003 | Turcott ............... 600/528 |
| 6,702,752 B2 | 3/2004 | Dekker |
| 6,804,551 B2 | 10/2004 | Griffin et al. |
| 6,805,673 B2 | 10/2004 | Dekker |
| 7,024,234 B2 | 4/2006 | Margulies et al. |
| 7,117,032 B2 * | 10/2006 | Childre et al. ............... 600/545 |
| 7,160,253 B2 * | 1/2007 | Nissila ............... 600/500 |
| 2002/0095092 A1 | 7/2002 | Kondo et al. |
| 2003/0036685 A1 | 2/2003 | Goodman |
| 2003/0163034 A1 | 8/2003 | Dekker |
| 2005/0124906 A1 * | 6/2005 | Childre et al. ............... 600/529 |
| 2005/0251054 A1 | 11/2005 | Zhirnov et al. |
| 2006/0052720 A1 | 3/2006 | Ross et al. |
| 2007/0021673 A1 | 1/2007 | Arbel et al. |
| 2007/0161912 A1 * | 7/2007 | Zhang et al. ............... 600/483 |
| 2007/0270668 A1 * | 11/2007 | Childre et al. ............... 600/300 |
| 2007/0299354 A1 * | 12/2007 | Striepe et al. ............... 600/509 |
| 2008/0045844 A1 * | 2/2008 | Arbel et al. ............... 600/484 |
| 2009/0076399 A1 * | 3/2009 | Arbel et al. ............... 600/500 |

FOREIGN PATENT DOCUMENTS

| | | |
|---|---|---|
| EP | 0534022 | 3/1993 |
| EP | 0666056 | 8/1995 |
| EP | 1419730 | 5/2004 |
| EP | 1 813 187 | 8/2007 |
| WO | WO 00/15106 | 3/2000 |
| WO | WO 02/26117 | 4/2002 |
| WO | WO 2004/019778 | 3/2004 |
| WO | WO 2004/026101 | 4/2004 |
| WO | WO 2004/052196 | 6/2004 |
| WO | WO 2009/024967 | 2/2009 |

OTHER PUBLICATIONS

Davies LC et al. , "A noninvasive measure of baroreflex sensitivity without blood pressure measurement", Am. Heart J., Mar. 2002, 143:441-7.

T. Kuvin et al., "Assessment of peripheral vascular endothelial function with finger arterial pulse wave amplitude Jeffrey", Israel Am. Heart J., 2003, 146:168-74.

Nurnberger J. et al., "Augmentation index is associated with cardiovascular risk", J. Hypertens, Dec. 2002, 20:2407-14.

Katz A. et al., "A simple bedside test of 1-minute heart rate variability during deep breathing as a prognostic index after myocardial infarction", Am. Heart J., Jul. 1999, 138: 32-8.

Singh N. et al., "Heart rate variability assessment after acute myocardial infarction: pathophysiological and prognostic correlates", Circulation, 1996, 93:1388-95.

Ponikowski P. et al., "Reproducibility of heart rate variability measures in patients with chronic heart failure", Clin. Sci., 1996, 91:391-8.

International Search Report of Application No. PCT/IL05/00095 Dated Dec. 15, 2005.

International Search Report of Application No. PCT/IL2008/001131 Date of mailing of international search report Jun. 22, 2009.

International Search Report for International Application No. PCT/IL2009/000788 Date of mailing Dec. 3, 2009.

* cited by examiner

METHOD AND SYSTEM FOR CARDIOVASCULAR SYSTEM DIAGNOSIS

CROSS-REFERENCE TO RELATED APPLICATIONS

This application is a continuation-in-part application of U.S. patent application Ser. No. 11/892,256, filed Aug. 21, 2007, entitled "Method and system for cardiovascular system diagnosis", which is a continuation-in-part application of U.S. patent application Ser. No. 11/489,721, filed Jul. 20, 2006 entitled "Method and system for cardiovascular system diagnosis", which in turn is a continuation-in-part application of International Application No. PCT/IL2005/00095, filed Jan. 27, 2005, which claims benefit of U.S. Provisional Patent Application No. 60/539,117, filed Jan. 27, 2004, all of which are incorporated in their entirety herein by reference.

FIELD OF THE INVENTION

The present invention relates to a method and system for diagnosing and monitoring the cardiovascular system. More particularly, the invention relates to a method and system for diagnosing and monitoring the cardiovascular system of a subject by analyzing the response of the cardiovascular system to a controlled stimulation protocol.

BACKGROUND OF THE INVENTION

Heart rate is controlled by a part of the Autonomic Nervous System (ANS) known as the cardiac autonomic system (parasympathetic and sympathetic activity). Heart Rate Variability (HRV) is a measure of the beat-to-beat variability of a subject's heart rate and provides a valuable noninvasive mean for evaluating the functioning of the cardiac autonomic system. It is known that HRV measurement can be used for assessment of cardiac autonomic status, and that disease severity in heart failure can be assessed via continuous 24 hour HRV measurement.

Assessment of HRV from 24-hour Holter ECG (a portable ECG monitoring device) recordings has sometimes been of prognostic value in patients after Myocardial Infarction (MI) ("*Heart rate variability assessment after acute myocardial infarction: pathophysiological and prognostic correlates*.", Singh N. et al. Circulation 1996; 93:1388-95) and in Congestive Heart Failure (CHF) patients ("*Reproducibility of heart rate variability measures in patients with chronic heart failure.*" Ponikowski P. et al, Clin. Sci. 1996; 91:391-8). However, this test is burdensome and does not provide quick results. According to a recent study, measures of HRV under physiologic stress (head-up-tilt) were able to differentiate between healthy control subjects and subjects with asymptomatic left ventricular dysfunction.

It is also known that the reproducibility of HRV in patients with CHF is poor (Ponikowski P. et al). As the clinical state of a patient deteriorates, although intrinsic HRV will fall, the standard measure of HRV does not reflect this fall because of the rise in ectopic beat frequency, which increases the degree of variability.

Reduced HRV during a single deep breath, or 1-2 minutes of repeated slow (0.1 Hz) breathing has been used as a measure of cardiac autonomic dysfunction for many years. It was shown to be better at differentiating between subjects with and without diabetes mellitus than the differences between horizontal and standing HRV and the Standard Deviation of Normal-Normal R-R intervals (SDNN), ("*A simple bedside test of 1-minute heart rate variability during deep breathing as a prognostic index after myocardial infarction.*", Katz A. et al. Am. Heart J. 1999 Jul. 138:32-8).

US 2004/0059236 to Margulies Lyle Aaron et al., describes physiological monitoring for detection of ANS activity during sleep. This publication teaches detection of frequent brief micro arousals by a pulse oximetry and EEG methods. ANS changes are determined by analyzing changes in the slope variations of the rising edge of the pulsatile blood volume waveform.

U.S. Pat. No. 6,319,205 and U.S. Pat. No. 6,322,515 to Daniel A. Goor et al., describes non-invasive detection and monitoring of a physiological state or medical condition by monitoring changes in the peripheral arterial vasoconstriction in reaction to such state or condition. Changes related to cardiopulmonary distress and blood pressure are monitored in order to detect or monitor physiological state or medical condition. A test is carried out with a finger probe capable of applying a pressure on the finger by a pressurizing cuff. In this way blood pooling in the veins at the measuring site can be prevented during the test.

EP 1419730 to Dehchuan Sun et al., describes a non-invasive apparatus for monitoring the side effects to the ANS caused by drugs used to prevent acute or chronic side effects to the brain nerves, and for monitoring the aging of nervous system by measuring the "physiological age" of the patient based on the ANS. Artery sphygmograms, or heart potential electric wave signals are obtained using a sensor and analyzed. HRV parameters are calculated by spectral analysis methods such as Fourier Transform.

US2003163054 to Andreas Lubbertus Aloysius Johannes Dekker describes monitoring patient respiration based on a pleth signal. The pleth signal is analyzed to identify a heart rate variability parameter associated with respiration rate.

The prior art fails to provide simple and rapid (about 1 minute long) noninvasive methods and systems for analyzing the status of the cardiovascular system, and in particular of the coronary blood system.

It is therefore an object of the present invention to provide a noninvasive method and system for quickly diagnosing and monitoring the cardiovascular system, and in particular the coronary blood system and cardiac ischemia of a subject based on the response of the blood flow to stimulation.

It is another object of the present invention to provide a method and system for processing and analyzing the response of the blood flow to stimulation in order to indicate the physiological condition of a subject.

It is a further object of the present invention to provide a method and system for quickly diagnosing and monitoring the cardiovascular system of a subject based on blood flow measurements.

It is a still another object of the present invention to provide a method and system for quickly diagnosing and monitoring the status of the cardiovascular system of a subject based on a test that can be performed anywhere and which does not require attendance of professionals.

Other objects and advantages of the invention will become apparent as the description proceeds.

SUMMARY OF THE INVENTION

It has now been found that it is possible to obtain valuable diagnostic information from blood Pulse Wave (PW) signals of a human subject during rapid excitation of the cardiovascular system of said subject. More specifically, the inventor of the present invention has devised a method and system for monitoring function and/or diagnosing dysfunction of the cardiovascular system of a human subject.

The method preferably comprise measuring PW signals of the subject during excitation of the cardiovascular system, analyzing the measured signals and computing indicators reflecting a response to said excitation.

The phrase PW signal is used herein to refer to a signal measured by a sensing device capable of sensing blood flow, volume, and/or pressure.

The phrase "excitation of the cardiovascular system" is used herein to indicate causing the cardiovascular system to increase its output and/or to experience load conditions or load simulation conditions.

In one preferred embodiment, the cardiovascular excitation may comprise a controlled breathing protocol characterized by a predefined frequency of breaths (e.g., about 0.1 Hz).

Optionally and conveniently, the pulse wave signals are measured at a peripheral region (e.g., body limb or extremity) including, but not limited to—an arm, a hand, a finger, ear, neck, wrist, leg, toe, ankle, chest, of the subject.

The method may further comprise segmenting the measured PW signals to distinct pulse waves. The segmentation is preferably carried out by finding a dominant frequency ($F_{heart}$) from the measured signals when transformed into the frequency domain, defining a scan window (W) according to the dominant frequency found (e.g., having a width of about $\frac{1}{3} \cdot F_{heart}$ or $\frac{1}{4} \cdot F_{heart}$), partitioning the PW signals into consecutive portions, the size of each is determined according to the scan window, finding a maximal value of said PW signal within each one of the portions, and finding a minimal value between pairs of consecutive maximal values found.

The method may further comprise calculating beat rate values by computing the inverse of the time difference between consecutive peaks (maximal values). A measure of the response to the excitation may be determined by performing time domain analysis, frequency domain analysis, and/or pulse wave morphology analysis to the measured PW signal.

Conveniently, the signals may be measured in a limb or extremity, including but not limited to an arm, a hand, a finger, ear, wrist, ankle, leg, toe, neck, or chest, of the subject. The computed indicators may include one or more of the following indicators: PWA range, AI, Pulse Period Range, HF integral, LF integral, BPM STDEV, PNN50, and BPM range, wherein said indicators are computed using signals obtained during the excitation and for normal pulse wave signals.

The PWA range indicator is the difference between the maximal and minimal values of the PW signal and it provides an indication of the response to excitation.

The AI (Augmentation Index) indicator provides a measure of the artery stiffness and is the calculated ration of two critical points on a pulse wave of the PW signal relative to an adjacent minimum value. These critical points are preferably found based on a forth derivative of the PW signal.

The Pulse Period Range is the range of variations of the time intervals of the pulse waves of the measured PW signals, and it provides an indication of ANS function.

The LF integral and HF integral indicators indicate sympathetic and parasympathetic effects on heart rate and are preferably calculated by using methods known in the art.

The BPM STDEV indicator is the standard deviation of the pulse rate (BPM series) computed from the measured signal. This indicator provides an indication of ANS function.

The BPM range is the difference between the maximal and minimal values in a beat rate series (BPM series) obtained from the measured signal. The BPM range indicated ANS function.

The pNN50 indicator is the percentage of the time intervals between consecutive peaks in the filtered PW signal which differs by more then 50 mS from a subsequent time intervals between consecutive peaks. This indicator provides an indication of ANS function.

The method may further comprise comparing the signals measured during cardiovascular excitation, and/or indicators computed therefrom, to the subject's normal blood flow or blood pressure signals (e.g., before applying the excitation), and/or indicators computed therefrom.

The method may further comprise extracting a Peripheral Flow Reserve (PFR) indicator by computing the ratio between averaged amplitude of the PW signal measured during the excitation and the averaged amplitude of normal blood PW signals of the subject.

The method may further comprise extracting a Respiratory Modulation Response (RMR) indicator by computing the ratio between a first and a second areas defined under the curve of the frequency domain representation of the PW signal. These areas are defined by two adjacent minimal values on said curve adjacently located on the two sides of the breath frequency. The first area is the area under said curve between the minimal values and the second area is the remainder obtained when subtracting the area under the line connecting the minimal values from the first area. It will be noted that Respiratory Modulation Response (RMR) may be referred to as Respiratory Stress Response (RSR) hereinafter and that RMR and RSR refer to the same indicator and may be used interchangeably hereinafter.

Preferably, a Responsive Augmentation Index Ratio (RAIR) indicator may be also extracted by computing the ratio between the AI indicator of the subject's normal blood PW signals and the AI indicator of the subject's responsive to the excitation.

The method may further comprise computing arterial flow, arterial stiffness, and ANS function, scores for indicating physiological functions, by calculating a weighted summation of the indicators. These scores may be used for computing a total score, wherein said total score is the linear combination of the scores. In addition, the scores may be manipulated for obtaining risk evaluations for one or more of the following cardiovascular events: acute coronary syndrome; sudden cardiac death; arrhythmia; stroke; and myocardial infarction.

According to another aspect the present invention is directed to a system for diagnosing and monitoring the function or malfunction of the cardiovascular system of a human subject. The system preferably comprise a sensor for measuring PW signals of a human subject, means for converting said signals into a data format, and a means for processing and analyzing the converted signals and extracting diagnostic indicators therefrom, wherein these signals are measured during excitation of the cardiovascular system of said subject.

The system may further comprise a low pass filter for separating breath offsetting components from the converted signals, and a means for subtracting these components from the converted signal.

Optionally, the system may further comprise an additional low pass filter for filtering out high frequency noise and an upsampler for interpolating the signal and thereby adding data thereto Preferably, the system further comprises means for comparing the PW signals measured during the excitation with the subject's normal PW signals, and for outputting corresponding indications accordingly.

Optionally, the processing mean of the system may be adapted to compute one or more of the following indicators:

PWA range, AI, Pulse Period Range, HF integral, LF integral, BPM STDEV, PNN50, and BPM range, RMR, PFR, and RAIR.

The invention may be used for one or more of the following applications: cardiovascular risk screening and assessment; cardiovascular intervention monitoring; cardiovascular intervention follow-up; and/or therapeutic strategy monitoring (including medications and life style changes such as diet and sports).

The invention may be used for diagnosing physiological dysfunctions such as: cardiac Ischemia, Endothelial dysfunction, coronary artery disease, coronary artery occlusion, arterial stiffness, autonomic nervous system dysfunction, myocardial infarction, and angina pectoris.

Optionally, the pulse wave signals may be measured invasively. The sensor may be selected from the group consisting of a Photoplethysmograph sensor; flow sensor; mechanical sensors; optical sensors, ultrasonic sensors; electrical impedance sensor.

DETAILED DESCRIPTION OF EMBODIMENTS OF THE INVENTION

While many attempts have been made to monitor cardiovascular functioning level by analyzing body surface signals, none has provided satisfactory results. When the various physiological systems are functioning at a steady state, much of their shortcomings are not revealed, however, when stimulated into an excited state, some of their dysfunction can be exposed. The present invention is based on the analysis of stimulated physiological systems response.

Controlled breathing at a frequency of 0.1 Hz stimulates the autonomic nervous system, and other physiological systems, such as the cardiovascular system (the blood system), and also tests the Baro-Reflex Sensitivity ("*A noninvasive measure of baro-reflex sensitivity without blood pressure measurement.*", Davies L C et al. Am. Heart J. 2002 Mar. 143:441-7). The HRV response to 0.1 Hz breathing was proved to be a predictor of death, following MI (Katz A. et al.). It was also shown that failure of the parasympathetic system is highly correlated to the risk of subsequent coronary events.

Studies have shown that the Augmentation Index (AI—a measure of the artery stiffness) is associated with cardiovascular risk ("*Assessment of peripheral vascular endothelial function with finger arterial pulse wave amplitude Jeffrey*" T. Kuvin et al. Israel Am. Heart J. 2003; 146:168-74), and that peripheral vascular endothelial function can be assessed by finger arterial pulse wave amplitude ("*Augmentation index is associated with cardiovascular risk.*" Nürnberger J. et al. J. Hypertens 2002 December 20:2407-14).

Figure 1:
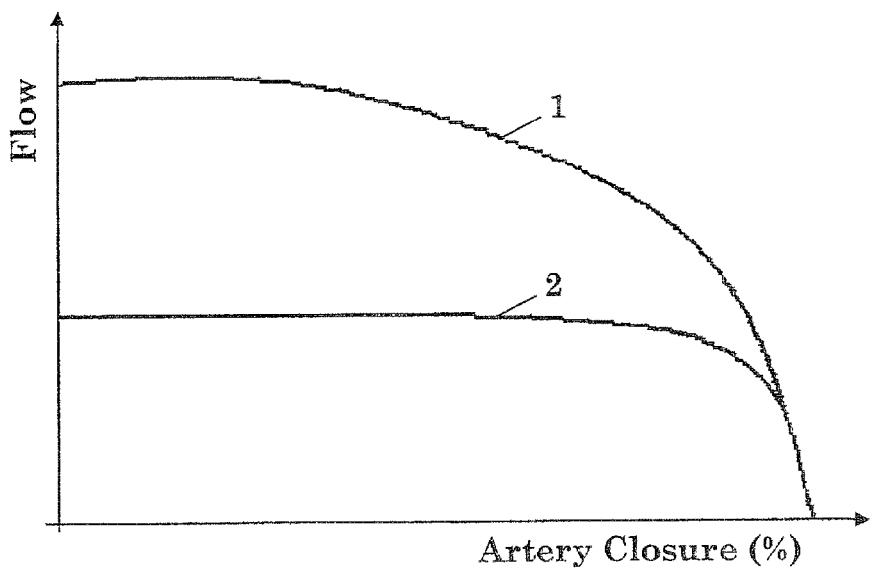
FIG. 1 graphically illustrates the changes in the blood flow during rest and during stimulation in different VB conditions.

The graph of blood flow as a function of artery closure shown in FIG. 1, demonstrates the blood flow of a normally functioning VB at a rest-state 2 and at a hyperemic-state (e.g., during stimulation) 1, which induces vasodilatation. As seen the blood flow in these states varies greatly, while for damaged (e.g. embolized, calcified or even partly dead) VB the blood flow at hyperemic-state 1 converges with the curve of flow at rest-state 2. Thus, the flow difference between these two states can be used to provide indications regarding both the ability of the vasculature to cope with increased flow demands, and also its general state of health. More specifically, it is expected that variability and an increased Pulse Wave Amplitude (PWA) will be observed between the patterns of the blood PW signal measured in a healthy subject at rest-state and during hyperemic-state stimulation, while the observation of negligible response (or even reduced PWA) to the stimulation indicates an unhealthy VB.

The VB auto regulation maintains a constant flow at rest for moderate arteries closure (Singh N. et al.; Nolan J. et al.). The flow at rest is determined by oxygen consumption and may be characterized according to artery diameter and auto regulating wall shear stress parameters. Correspondingly, the resistance of the VB is decreased in order to compensate for arterial closure and to preserve total vascular resistance in the rest-state. VB auto-regulation can maintain constant flow at rest-state only if the resistance of the VB is higher than the minimal VB resistance (resistance during maximal hyperemia). For severe arterial closure, VB resistance at rest-state is already minimal. If the difference between the signals measured at rest-state and hyperemic-state is insignificant, it is most probably since the cardiovascular system does not provide enough flow increase during the hyperemic-state.

As will be discussed in detail hereinafter, if the amplitude of the PW signals during the hyperemic-state does not increase significantly relative to PW signals obtained at the rest-state (baseline reference), the following diagnosis may be reached:
(i) blocked arteries;
(ii) a VB or myocardial problem; or
(iii) both VB problem and blocked arteries.

Figure 2:
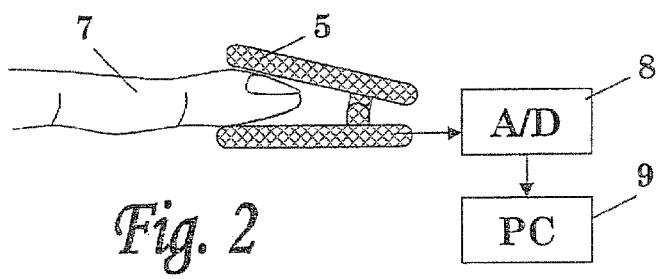
FIG. 2 schematically illustrates a system for measuring the PW signal and analyzing said signal according to the invention.

In an embodiment of the invention shown in FIG. 2, blood PW signals are obtained via a Photoplethysmograph (PPG) sensor 5 placed on the finger tip 7 of the tested subject. The PW signals are analyzed by comparing the PW signals obtained from the tested subject (7) by PPG sensor 5 at rest-state to the PW signals obtained during hyperemic-state. An analog-to-digital converter 8 is used for digitizing the signals received from the PPG sensor 5, and for providing the same to the PC (Personal Computer—Pocket PC, or any other means capable of reading the measured data, processing it, and outputting the data and the results) 9. The A/D 8 may be embedded in the PPG sensor 5 (e.g., Dolphin Medical Oximetry sensor) or in PC 9, or provided as an independent unit. Although each of the sensor 5, A/D 8, and PC 9, elements may be powered separately by a dedicated power supply, in the preferred embodiment of the invention the power supply of these elements is provided by PC 9.

It is of course difficult to determine from the flow changes as reflected by the PW signals measured by the PPG sensor 5, the cause of the problem (i.e., blocked arteries, VB, and/or myocardial problem). In order to distinguish between the above-identified determinations (i, ii, or iii) other criteria have been developed, and will be described in detail hereinbelow.

It should be clear that various types of sensors and signal acquisition systems can be used to acquire the pulse wave signals. PPG PW signals were found to be particularly preferable, due to the ease and simplicity of the measurement process. Other types of sensors that can be used include (but are not limited to): mechanical sensors, optical sensors, ultrasonic sensors or electrical impedance sensor. Specific examples of suitable devices include: finger mechanical plethysmograph—as developed by Itamar Medical (Itamar Medical Ltd., Caesarea, Israel); Carotid pressure wave plethysmograph—as developed by SphygmoCor (AtCor Medical Pty Ltd., NSW, Australi); Electrical Impedance plethysmograph as developed by cardiodynamics (Cardiodynamics International Corp., san diego, Calif.), Capillary (Skin) blood flow (SBF) as developed by I.S. MedTech (I.S. Medtech Ltd., Beer-Sheva, Israel), blood pressure cuff, or any other similar devices. The PC 9 may be any computerized (or analog) system that is able to receive input signals, process and analyze said signals, store and read data in/from memory(s) provided therein, and provide corresponding outputs for example via a graphical display unit (not shown). PC 9 can be a pocket-PC or a type of Personal Digital Assistance (PDA) device, or any other means capable of inputting measurements, performing calculations, and outputting results.

The sensor 5 may be attached to the patient (7), and he is relaxed and mentally prepared for the test. The test process is illustrated in the flowchart shown in FIG. 3. In the first step 30 the PW signals at a rest-state are recorded. The recorded rest-state signals define the patient's baseline signal and used as a reference for determining the response to stimulations. Next, in step 31 the cardiovascular system of the patient is stimulated. While it is possible to perform the measurements described in accordance with the present invention without stimulation of the subject, it has been found that results are significantly improved where stimulation was performed. Various stimulations techniques can be employed, most preferably, a controlled breathing at 0.1 Hz, which will be used hereinafter to demonstrate the invention. In the case of controlled breathing stimulation the patient is guided to breathe deeply according to visual or auditory signs (e.g., via display device or speakers of PC 9) or medical personnel instructions.

It should be noted, however, that according to embodiments of the invention, other methods for stimulating the cardiovascular system may be used. Detailed below are several illustrative non-exhaustive examples of methods of stimulating the cardiovascular system in accordance with the present invention. Other suitable stimulation methods are likewise applicable. For example, the stimulation may be reached by using a Brachial Artery Recovery (BRT) stimulation protocol where the brachial artery is blocked for a predetermined period, for example, several minutes, by a blood pressure cuff which may then be opened in order to analyze the reactive hyperemia response.

According to other embodiments of the invention, the cardiovascular system may be stimulated by periodic physical drills. A non-exhaustive list of possible periodic physical drills may include sit-ups, arm-waving, walking, and/or sitting/standing cycles. Yet other possible cardiovascular system stimulations may include facilitated periodic movements, whereby the subject's body may be harnessed to an external oscillator capable of causing the entire body or body parts to move in a cyclic or periodic fashion.

According to other embodiments of the invention, stimulating the cardiovascular system of a subject may include periodic visual stimulation, namely, subjecting the subject, for example, to periodically changing images or visual patterns, periodic auditory stimulation, namely, subjecting the subject, for example, to periodic sound or music or periodic pressure application where the body or body parts (in particular the thorax or the neck) may be subjected to periodic external pressure, by for example, pneumatic, hydraulic, or mechanical means. Heating cycles which may include alternating heating and cooling periods of body parts, especially the face, activating the mammal diving reflex may also be used for stimulating of the cardiovascular system.

According to some embodiments of the invention, stimulating the cardiovascular system of a subject may be performed, provided, achieved or caused by applying periodic pressure to the extraocular muscles. As known in the art, the oculocardiac reflex, also known as Aschner phenomenon or the Aschner reflex is the demonstration of a decrease of pulse rate associated with pressure or traction applied to the extraocular muscles. Such decrease of pulse rate may also be achieved by compression of the eyeball. According to embodiments of the invention, pressure application to an eyeball of the subject or contraction of the extraocular muscles of the subject may be applied periodically in order to control and/or stimulate the subject's cardiovascular system.

According to other embodiments of the invention, stimulating the cardiovascular system of a subject may be performed, provided, achieved or caused by repeatedly performing the Valsalva manoeuvre. As known in the art, the Valsalva maneuver may be performed by exhaling into a closed airway. As known in the art, the Valsalva maneuver may affect the autonomic nervous control of the heart and consequently affect the stimulation level of the associated cardiovascular system. According to other embodiments of the invention, excitation of the cardiovascular system may be provided or achieved by repeatedly performing the Valsalva manoeuvre.

According to other embodiments of the invention, stimulating the cardiovascular system of a subject may be performed, provided, achieved or caused by repeatedly performing the Muller manoeuvre. As known in the art, the Muller manoeuvre comprises inhaling while airways, e.g., nose and mouth are obstructed. As known in the art, changes of heart rate may be observed as a result of performing the Muller manoeuvre. Accordingly, embodiments of the invention may utilize a periodic or other performing of the Muller manoeuvre by the subject in order to provide, achieve, cause and/or maintain a stimulation of the subject's cardiovascular system.

In step 32 the PW signals during stimulation (hyperemic-state signals) are recorded (e.g., during the controlled breathing stimulation). The recorded, rest-state and hyperemic-state, PW signals (hereafter also referred to as raw-signals) are analyzed in step 33, and in step 34 internal indicators are extracted utilizing the processed signals. The internal indicators may include, but not limited to, indicators known in the art such as—PWA range, AI, HF integral, LF integral, BPM STDEV, PNN50, and BPM range. As will be explained herein later, such indicator can be used to determined the response of the cardiovascular system of the tested subject to the excitation. However, as will be explained hereinafter, new indicators particularly suitable for this invention were also developed for this purpose. The internal indicators are weighted and grouped to give 3 scores: a stiffness score 35, flow score 36, and ANS score 37. These scores can then be used to determine a total score 38, for assessing the status of the patient's cardiovascular system.

The rest-state signals acquired in step 30 can be measured, for example, during 10-100 seconds of spontaneous breathing, and the excitation-state signals acquired in steps 31-32 may be obtained during controlled breathing at a low and steady rate, for example, at a frequency of 0.1 Hz (5 seconds inspiration and 5 seconds expiration), for 30-300 seconds (e.g., 3-30 cycles of 10 s each).

According to a preferred embodiment of the invention the first steps of the test process (steps 30 to 33) are performed within a 90 seconds time interval, including 20 seconds of spontaneous breathing (step 30), to set the baseline reference, and 70 seconds (steps 31 and 32) of guided deep breathing at a low and steady rate of 0.1 Hz (namely, 7 cycles, 10 seconds each, comprising 5 seconds of inspiration and 5 seconds of expiration).

The rest-state PW signals obtained in step 30 are used as a baseline reference characterizing the normal state of the patient's cardiovascular system (CV). The rest-state PW signals obtained in step 30 and the hyperemic-state PW signals obtained in steps 31-32 are analyzed using time domain analysis for finding the beat-to-beat heart rate series and heart cycles series, and for extracting indicators 34 and computing scores 35-38 therefrom. Frequency domain analysis (e.g., FFT—Fast Fourier Transform) is used for finding the power spectrum of the signal at several frequency bands and extracting additional indicators 34. Pulse Wave morphology analysis is also used in order to extract more indicators, regarding endothelial dysfunction and arterial stiffness (the inability of a blood vessel to change its volume in response to changes in pressure). The indicators 34 may be combined to indicate performance level of physiological functions.

Figure 4:
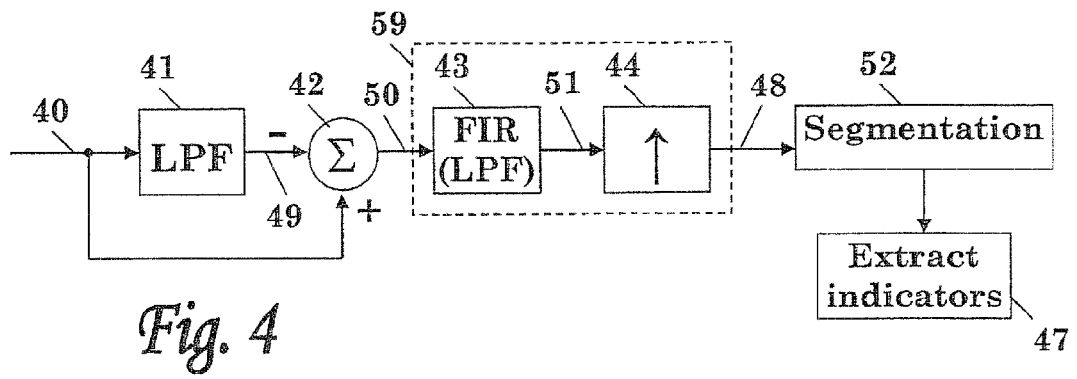
FIG. 4 is a block diagram illustrating the signal processing and analysis of the measured flow pulse signal.

FIG. 4 is a block diagram illustrating the signal processing and analysis and indicator extraction performed in steps 33-34 of the test process. The measured raw-signal 40 is filtered by a Low-Pass-Filter (LPF) 41, for extracting the breath-curve signal 49. LPF 41 is preferably a second order resonant LPF with a cut-off frequency of about 0.15 Hz. Subtractor 42 is used to subtract the breath-curve signal 49 from the raw-signal 40, thereby providing a non-modulated (i.e., without offsetting components) PW signal 50. Signal processing elements, LPF 41, and subtractor 42, may be implemented by software, and/or utilizing suitable of-the-shelf hardware devices. Alternatively, a dedicated Digital Signal Processing (DSP) device is used for this purpose. However, in a preferred embodiment of the invention the signal processing elements are implemented by software, and all the processing and analysis steps (33-38) are performed by the PC 9.

It may be desired to upsample the non-modulated signal 50. If so, the signal may optionally be filtered by LPF (e.g., FIR—Finite Impulse Response) 43 for removing interfering noise (e.g., above 8 Hz), and then upsampled by upsample unit 44, as shown in the dashed box 59.

The obtained signal 50 (or 48 if upsample unit 59 is used) can be used for calculating various indicators (47), as will be explained in detail hereinbelow.

The calculation of the Peripheral Flow Reserve (PFR) indicator can be carried out according to the following equation:

$$PFR = \overline{Q_{hyper}} / \overline{Q_{rest}}$$

where $\overline{Q_{hyper}}$ is the average of the Pulse Wave Amplitude (PWA) of the processed signal corresponding to the hyperemic-state (steps 31-32), and $\overline{Q_{rest}}$ is the PWA average of signal corresponding to the rest-state (step 30).

It has been shown that the main flow parameters of the arterial auto regulation (the intrinsic ability of an organ to maintain a constant blood flow despite changes in perfusion pressure) in the peripheral arteries are similar to those of the coronary system. This may be used to provide diagnosis concerning the cardiovascular system of the tested subject.

Figure 9A:
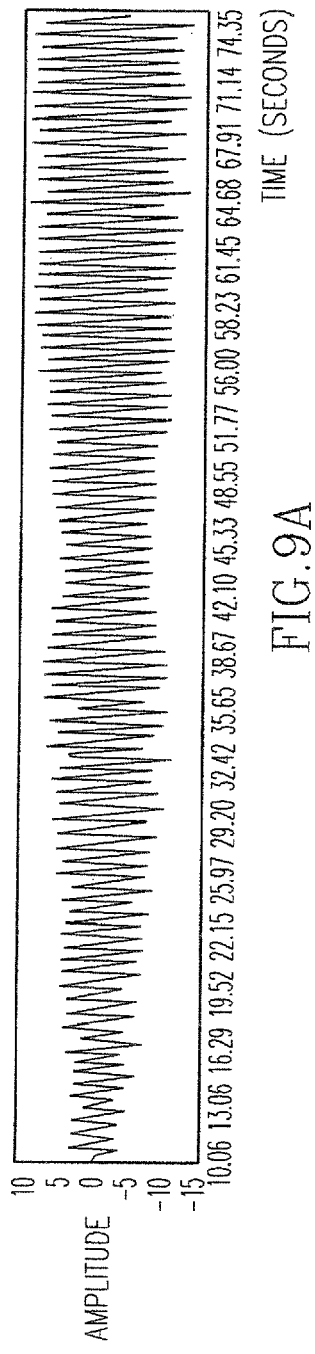
FIGS. 9A-9C graphically shows processed pulse wave signals demonstrating different conditions of patients' cardiovascular system and VBs (healthy, embolized, calcified)

There are three major indications that can be observed in the changes of the amplitude of the measured PW signal, for example:

Healthy cardiovascular system allows significant increase of flow rates as a response to an excitation exercise (i.e., hyperemic-state) and this increase is manifested in a steady increase in the amplitude of the measured PW signal, as exemplified in the non-modulated PW signal shown in FIG. 9A.

Figure 9B:
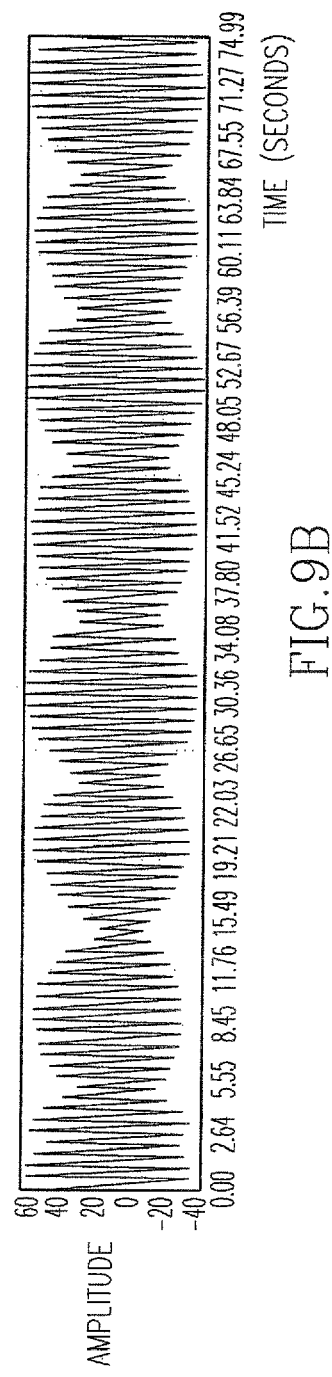

If the VB is partly damaged, it can not expand enough to allow significant increase of the blood flow in the hyperemic-state. In this case, the shape of the PW signal measured during the rest-state will be similar to the shape of the PW signal measured during hyperemic-state, exemplified in the non-modulated PW signal shown in FIG. 9B. However, the arteries in this case are not blocked and endothelial function of the larger arteries is still at least partly active.

Figure 9C:
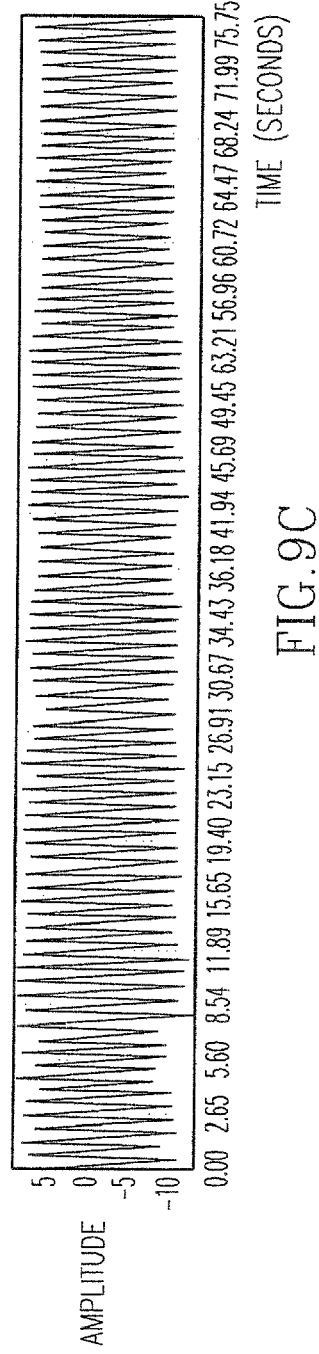

If the VB and endothelium function of larger arteries are damaged, the system can not expand enough to allow significant increase of the blood flow in the hyperemic-state, as exemplified in the non-modulated PW signal shown in FIG. 9C. Some of the arteries are probably blocked, so instead of the expected healthy increase in the amplitude of the pulse waves, as seen in FIG. 9C, the amplitude of the pulse waves may even be decreased.

The processed signal may be partitioned into distinct pulse segments in block 52. The segmentation can be carried out utilizing conventional methods known in the art.

Figure 5:
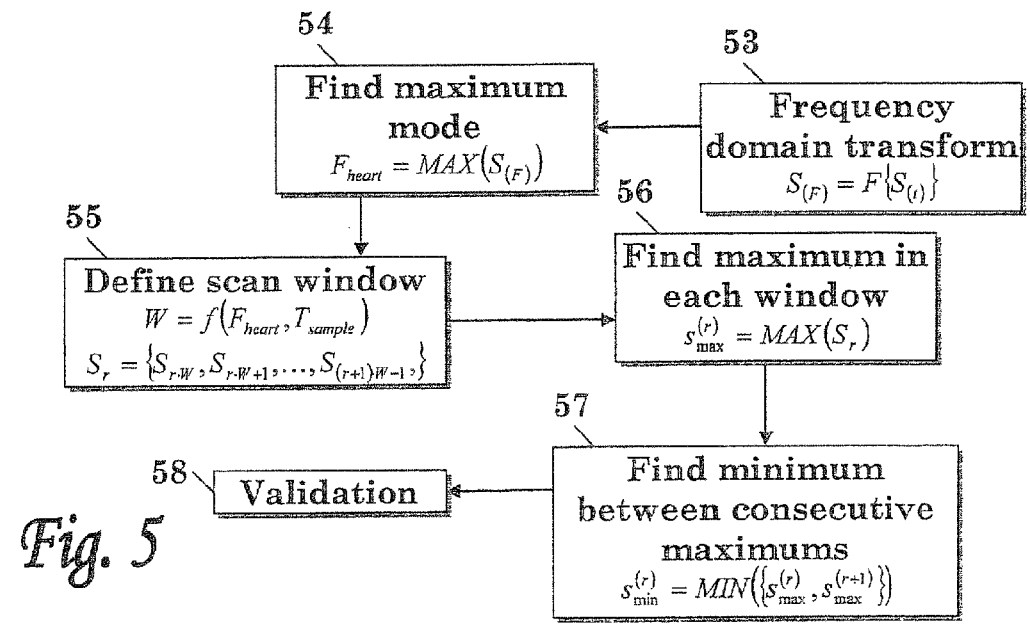
FIG. 5 is a flowchart illustrating a preferable process for pulse wave segmentation.

FIG. 5 is a flowchart illustrating a preferable process for pulse wave segmentation (52). This process starts in step 53 wherein a frequency transformation is applied to the measured time-domain PW signal $S_{(t)}$, thereby transforming it into the frequency domain, $S_{(F)} = F\{S_{(t)}\}$. In step 54 the frequency $F_{heart}=MAX(S_{(F)})$ is determined from the spectrum of the PW signal $S_{(F)}$. $F_{heart}$ and the sampling time $T_{sample}$ are used in step 55 to define a scan window $W=f(F_{heart}, T_{sample})$. The temporal width of the scan window is preferably set to about $\frac{1}{3} \cdot F_{heart}$ or $\frac{1}{4} \cdot F_{heart}$ and the number of samples in the scan window is defined by the sampling time $T_{sample}$. The scan window is used to partition the time-domain PW signal $S_{(t)}$ into a number of sections $S_{(t)}=\{s_0, s_1, \ldots, s_{W-1}\}$, $\{s_W, s_{W+1}, \ldots s_{2W-1}\}, \ldots, \{s_{r \cdot W}, s_{r \cdot W+1}, \ldots s_{(r+1) \cdot W-1}\}$ (r=0, 1, ...). In step 56 the maximal value $s_{max}^{(r)}=MAX(S_r)$ in each section $S_r=\{S_{r \cdot W}, S_{r \cdot W+1}, \ldots, S_{(r+1) \cdot W-1}\}$ is found, and in step 57 the minimal value $s_{min}^{(r)}=MIN(\{s_{max}^{(r)}, s_{max}^{(r+1)}\})$ between each consecutive maximal values $\{s_{max}^{(r)}, s_{max}^{(r+1)}\}$ is found. In this way the maximum (the peak) points (75 in FIG. 7), and the minimum points (73) on the curve of each pulse wave are determined.

This process terminates in a validation step 58, in which the validation of the width and height of the found pulse waves are checked according to various criteria. For example, pulse waveforms width validation can be performed by calculating time length between consecutive peaks and the slope of the peak systole. The widths are tested by checking the distances between the peaks, which should be within a predefined range (e.g., 40%) about the median width. Similarly, validation of the pulse heights (i.e., the amplitudes of each maximal value) can be performed.

The beats per minute (BPM) series is extracted from the PP Series which is comprised of the time intervals between consecutive peaks in the PW signal (e.g., $Ts_{max}^{(r+1)}-Ts_{max}^{(r)}$).

Figure 6:
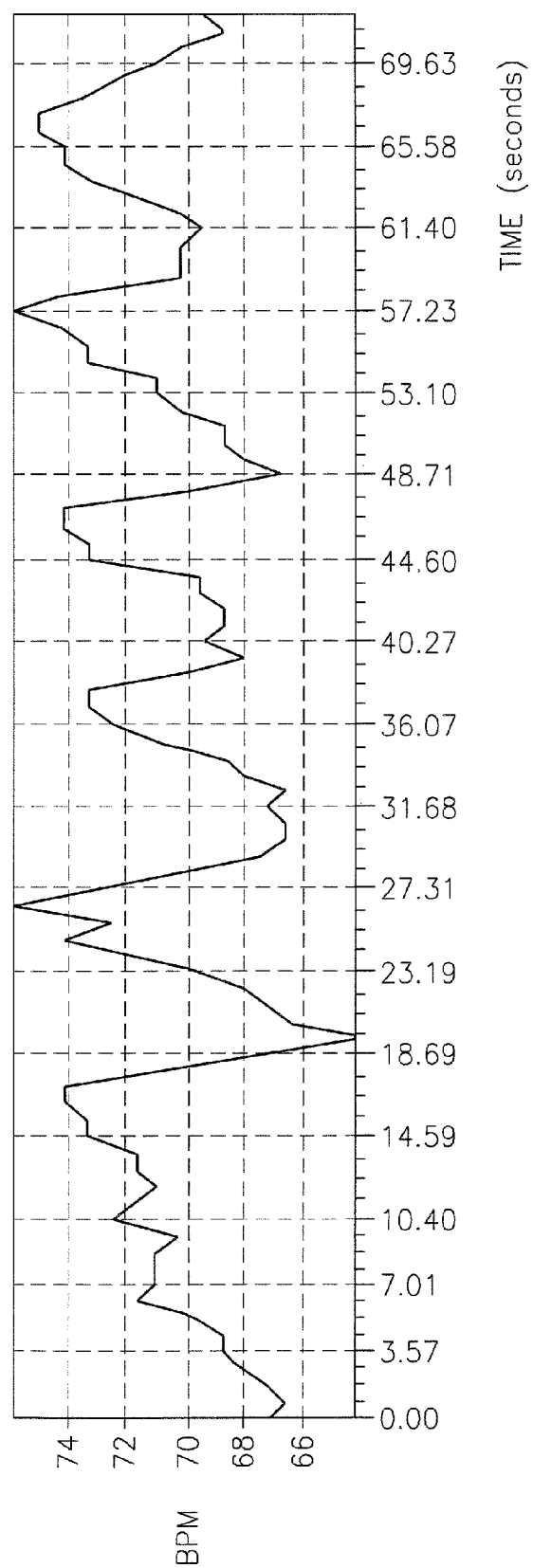
FIG. 6 shows a graphical presentation of the HRV obtained from a measured PW signal.

FIG. 6 graphically shows a BPM series extracted from the pp series. The BPM series is obtained by inversing time intervals between the pulse waves ($1/T_{PW}^{(0)}$, $1/T_{PW}^{(1)}$, $1/T_{PW}^{(2)}, \ldots$ where $T_{PW}^{(r)}=Ts_{max}^{(r+1)}-Ts_{max}^{(r)}$). The BPM therefore shows the variability of the heart rate over time.

Figure 7:
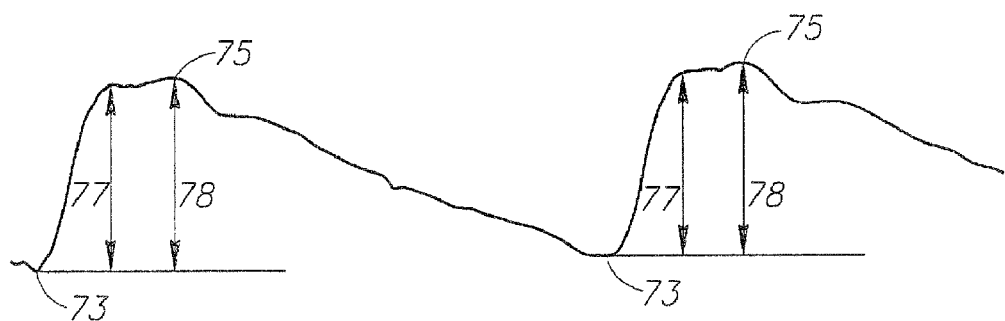
FIG. 7 graphically demonstrates calculation of the augmentation index.
Figure 8:
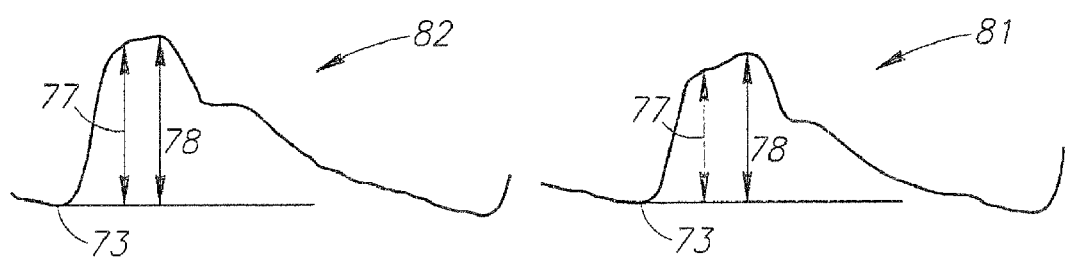
FIG. 8 graphically demonstrates the change of the augmentation index in hyperemic state.

The AI indicator is calculated based on a method described by Takazawa, K., et al. ("*Assessment of vasoactive agents and vascular ageing by the second derivative of photoplethysmograph waveform*", 1998, Hypertension 32, 365-370). FIGS. 7 and 8 graphically demonstrates the calculation of the AI for each pulse wave of the PW signal $S_{(t)}$. The magnitudes 77 ($PT_1$) and 78 ($PT_2$) of two critical points relative to the adjacent minimum 73 value are found based on a forth derivative of the PW signal ($\partial^4 S^{(t)}/\partial t^4$). The AI is obtained by calculating the ration—$AI=PT_2/PT_1$. As shown in FIG. 8, the geometry of the pulse waves is normally changed during the hyperemic-state 81, in comparison with that measured in the rest-state 82. This change will be indicated by an increase in the AI value.

The AI indicator provides a measure of the artery stiffness. AI values in the range 0.5 to 0.8 generally indicate good artery stiffness, while AI values in the range 1 to 1.3 generally indicates vasculature dysfunction.

It is helpful to define a Responsive Augmentation Index Ratio (RAIR), which indicates the large peripheral artery endothelial response to excitation. This indicator can be calculated in a way similar to the calculation of the PFR, namely the ratio of the AI at hyperemic-state ($AI_{Hyper}$) to the AI at the rest-state ($AI_{rest}$), $RAIR=AI_{Hyper}/AI_{rest}$.

The AI and RAIR indicators can be extracted from a calculated average pulse wave (i.e., by averaging samples of numerous pulse waves), or alternatively by computing the average AI value of numerous pulse waves.

Figure 10A:
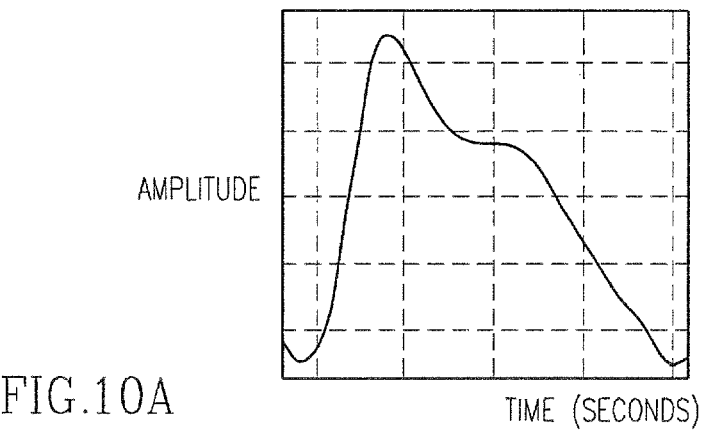
FIGS. 10A-10C demonstrates few diagnostic determinations deduced from the geometry shape of pulse waves.
Figure 10B:
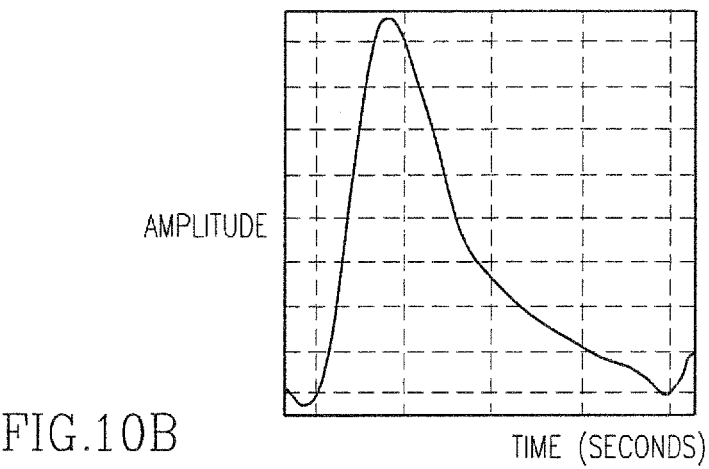
Figure 10C:
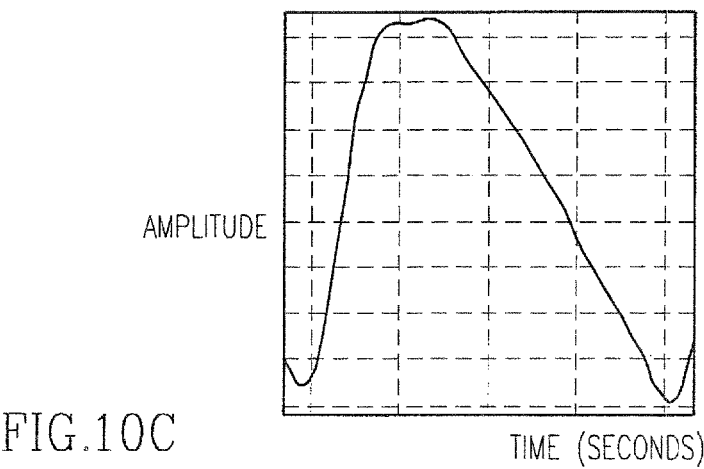

Inspection of the geometry of the pulse waves shown in FIGS. 10A-10C can lead to the following determination:

FIG. 10A—low artery stiffness and low AI (AI~0.5-0.8). This pulse wave was extracted from the non-modulated PW signal shown in FIG. 9A, for which a healthy increase in the amplitude of the pulse waves was observed.

FIG. 10B—medium AI(AI~0.8-1.0), indicating the beginning of arterial stiffness and endothelial dysfunction. This pulse wave was extracted from the non-modulated PW signal shown in FIG. 9B, for which an insignificant response was observed in the hyperemic-state.

FIG. 10C—high AI (AI~1-1.3), indicating high artery stiffness and low endothelium function. This pulse wave was extracted from the non-modulated PW signal shown in FIG. 9C, which was taken from a subject suffering from blocked arteries and problematic VB (embolized or calcified).

Additional observations for assessing the arterial flow response of a tested subject are attained from frequency domain analysis of the PW signal measured during the test. In this analysis the spectrum $S_{(F)}$ (e.g., FFT, wavelet) of the measured PW signal $S_{(t)}$ is analyzed. An additional indicator, RSR, is extracted in this analysis, as exemplified in FIG. 12. The Respiratory Modulation Response (RSR) provides indications concerning the cardiovascular and autonomic nervous systems response to the stimulation.

The RSR provides a measure of the influence of modulating excitation (e.g., breath excitation) on the measured PW signal. In the preferred embodiment of the invention the RSR is equal to the area of the respiratory peak (The peak around the 0.1 Hz frequency) in the power spectrum of the monitored signal, and is calculated as follows:

The area under the power spectrum curve between two adjacent minimal values (e.g., ($S_{(fm1)}$ and $S_{(fm2)}$)) on said curve adjacently located on the two sides of the excitation frequency (e.g., 0.1 Hz breath frequency) (e.g., $S_{(fm)}$) is divided into two areas:

(I)—The total peak area ($A_{Total}=A_{DBE}$); and (II) the area below the 'AC' line ($A_{DACE}$—in FIG. 12). Where the 'AC' line is the line connecting two adjacently located minimums ($S_{(fm1)}$ and $S_{(fm2)}$) of the spectrum, as shown in FIG. 12).

Figure 12:
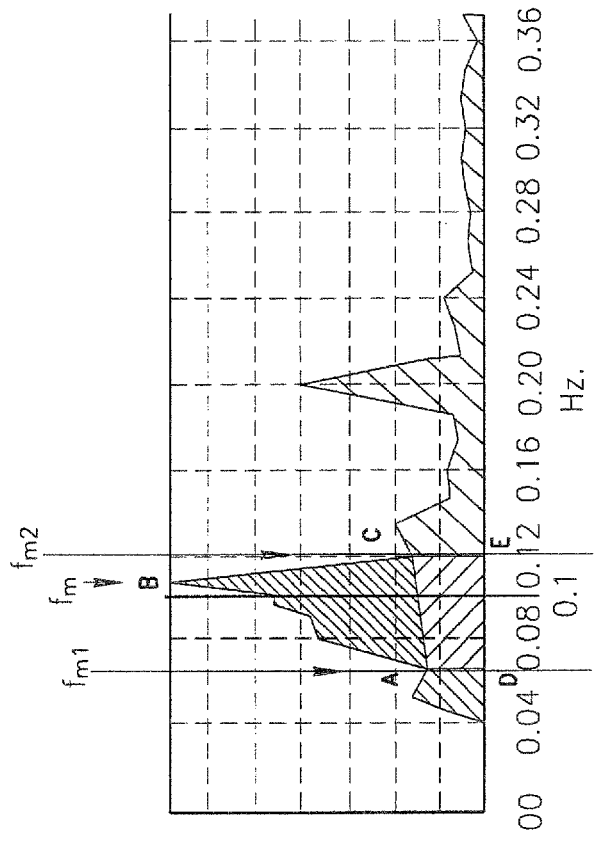
FIG. 12 demonstrate computation of the respiratory modulation response indicator from the frequency transformation of a measured PW signal.

According to some embodiments of the invention, points A and C defining the 'AC' line as shown in FIG. 12 may be determined according to various calculations, methods or algorithms. For example, point C may be determined by first identifying point B that may be the peak around the 0.1 Hz frequency as shown in FIG. 12 or another selected frequency, and further moving up the frequency scale up to a point where the slope of the power spectrum curve is smaller than or below a predefined value. For example, a first derivative may be computed over a series of points along the power spectrum curve and point C may be determined as the point where the absolute value of such derivative starts to decrease and where further becomes smaller than a predefined value. Accordingly, point A may be determined in a similar or analogous manner. Alternatively or additionally, various other parameters, conditions or constraints may be used to locate or determine points A and C.

According to embodiments of the invention, a number of conditions may be concurrently observed and points A and C may be located when one or more such condition are met. For example, two, possibly different respective maximum distances of points A and C from the peak around a chosen frequency, e.g., point B, may be predefined. Accordingly, possibly in addition to observing the slope, slant or gradient of the power spectrum curve as described above, the distance from point B may be observed and accordingly, a location of points A and C may be determined by either reaching a predefined distance from point B or by observing a predefined slope or gradient.

It will be noted that the predefined value and/or parameters used for locating points A and C, e.g., a minimum or maximum gradient of the power spectrum curve or a maximum distance from point B as described above may be configurable. For example, such predefined values may be manually set by a user or they may be dynamically determined or computed by software according to various aspects and/or parameters of the power spectrum curve. Alternatively or additionally, such predefined parameters may be computed and/or defined based on medical or other information pertaining to the subject being tested and/or any other applicable information, data or parameters.

The RSR is then obtained by the following calculation:

$$RSR1 = \frac{A_{Total} - A_{DACE}}{A_{Total}}.$$

For example, RSR may be computed as follows:

$$RSR = \frac{\left(\int_{f_{m1}}^{f_{m2}} S_{(F)} \cdot d_F\right) - \frac{1}{2}(S_{(f_{m1})} + S_{(f_{m2})})(f_{m2} - f_{m1})}{\int_{f_{m1}}^{f_{m2}} S_{(F)} \cdot d_F}$$

RSR values in the range 30% to 100% generally indicate good cardiovascular response, while AI values below 30% generally indicates a cardiovascular dysfunction.

Figure 19:
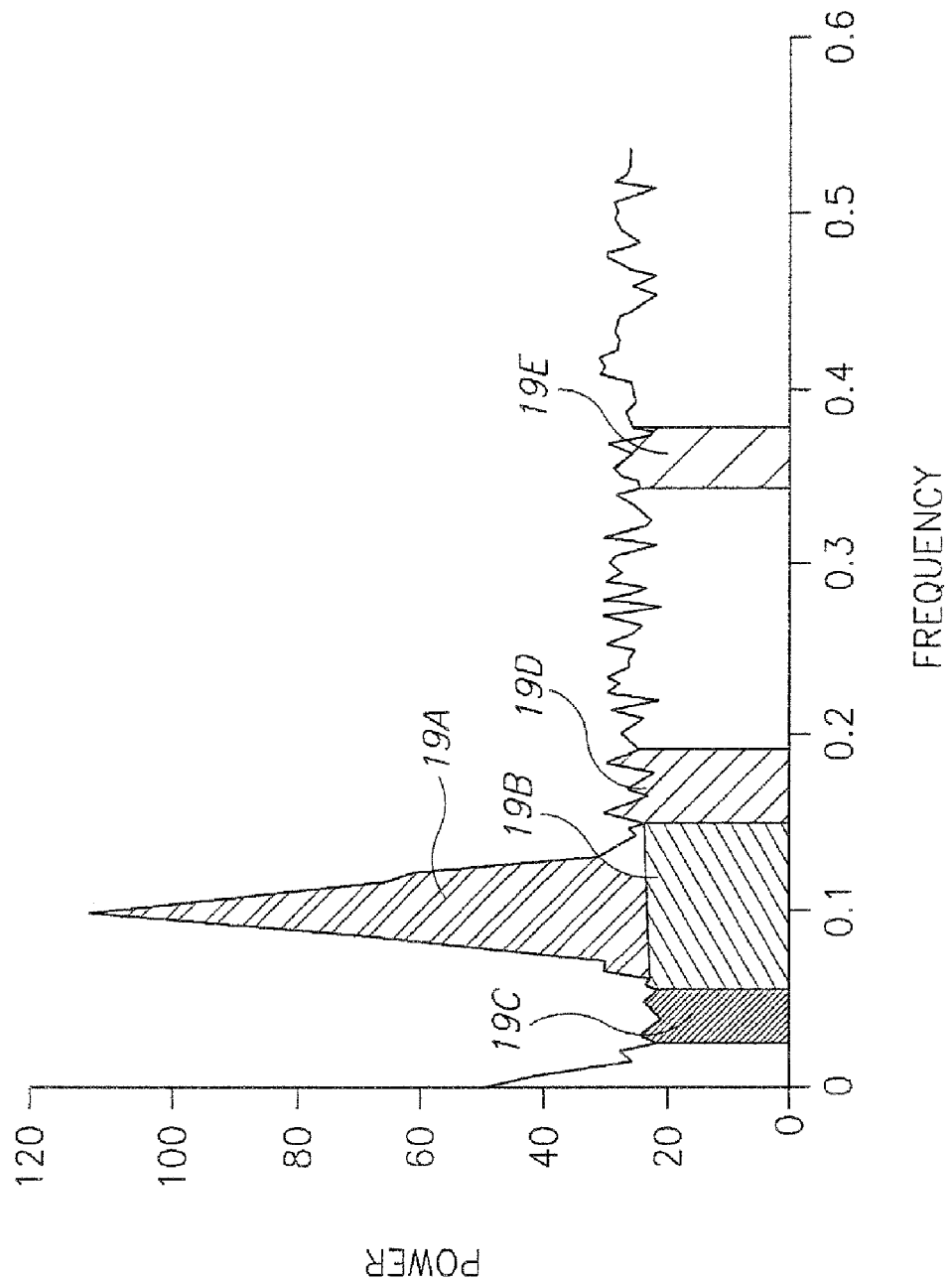
FIG. 19 shows an illustration of a power spectrum showing portions of the area that may be used for calculating RMR indicators according to embodiments of the invention.

It will be noted that while RSR according to one embodiment of the invention has been described above, other measures of respiratory modulation response may be calculated and compared to suitable ranges of values. For example, in other embodiments of the invention, areas in the frequency domain including or representing response to stimulation may be compared to areas representing status quo. Reference is now made to FIG. 19 showing exemplary areas 19A, 19B, 19C, 19D, and 19E that may be used for calculating RMR indicators For example, the following exemplary calculations may be used:

$$RSR = \frac{19A + 19B}{19A} \text{ or}$$

$$RSR = \frac{19A + 19C + 19D}{19A} \text{ or}$$

$$RSR = \frac{19A}{19E}.$$

It will be noted that other calculations involving areas 19A, 19B, 19C, 19D and 19E may be used, for example, the inverse of any of the above equations may be used as an RMR indicator. Furthermore, other suitable areas in the power spectrum shown in FIG. 19 may be defined and used for calculating RMR indicators.

Figure 11A:
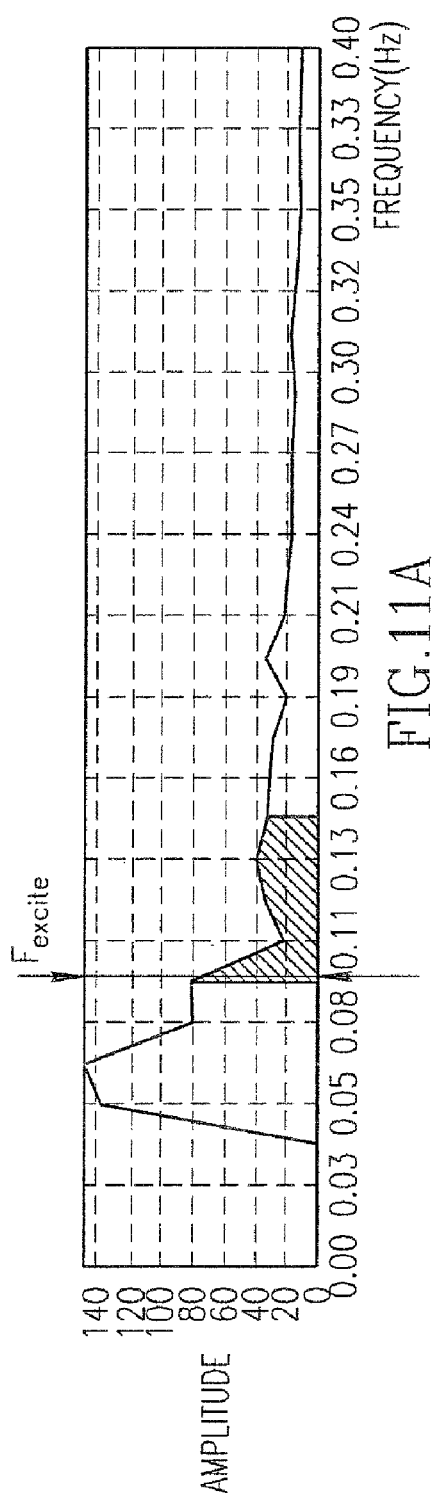
FIGS. 11A-11B demonstrates frequency domain analysis of signals measured according to the invention.
Figure 11B:
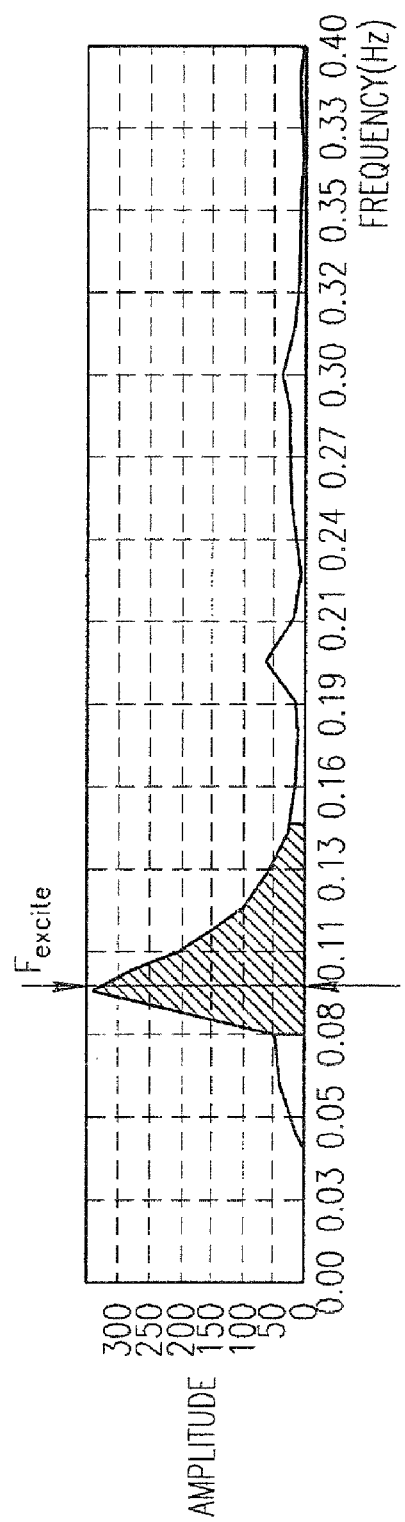

FIG. 11A graphically illustrates the spectrum of the PW signal of a subject tested according to the test process of the invention. In this example, the tested subject performed the 0.1 Hz controlled breathing excitation. As seen there is a weak response (negative RMR). FIG. 11B graphically illustrates the spectrum of the PW signal of the same subject tested according to the test process of the invention after a stenting procedure (PTCA—Percutaneous Transluminal Coronary Angioplasty). As seen there is a strong response about the frequency of the breathing excitation $F_{ecxite}$ (0.1 Hz), which indicates an improvement in the coronary flow due to the stenting procedure.

According to some embodiments of the invention, an RMR indicator may be computed for a cardiovascular system without stimulation. As known in the art, a cardiovascular system may naturally or inherently have a resonant frequency around 0.1 Hz. For example, a human cardiovascular system may exhibit low-frequency arterial pressure oscillations and resonate around a well known frequency, a phenomenon known as Mayer's waves. Such oscillations may produce a peak in the power spectrum, such peak may be used as described above for the computation of an RMR indicator. According to some embodiments of the invention, measurement of a subject's breaths signals and the respective pulse wave (PW) signals may be obtained, a breathing period may be defined, for example as the peak to peak time interval, and a breathing frequency may be defined as the inverse of the defined period. Next a sequence of breaths may be selected such that none of the breaths' period deviates from the conjoint average period of the selected sequence by a predefined value, for example, by 10% of the conjoint average period. Selecting the sequence of breaths such that the conjoint average period's frequency is within a proximity of the natural resonance frequency of the cardiovascular system in question may yield a peak in the power spectrum of the respective PW. Such peak may be used as described above for the computation of an RMR indicator. It should be noted that RMR measures can be obtained utilizing spectral analysis other than FFT (e.g., wavelet transform). Moreover, the RMR may be obtained by a time domain analysis of the measured PW signal.

According to some embodiments of the invention, proper execution of a controlled breathing protocol may be verified and/or validated prior to beginning analysis. According to some embodiments of the invention, validation and/or verification that the acquired data may be used for calculating indicators such as, but not limited to, a RMR indicator, may be performed. In some embodiments of the invention, such verifications may be performed before analyzing the measured signals and/or computing various indicators. In some embodiments, the verification may be performed after analysis, for example, based upon a fault indication.

A mandated breathing protocol or regimen, such as controlled, possibly slow, breathing, particularly at a desired frequency, is likely to cause respiratory modulation of the heart rate, and consequently, may result in a power peak in a corresponding power spectrum of a BPM waveform. According to some embodiments of the invention, verification of proper execution of a controlled breathing protocol may be performed by first computing a power spectrum of a BPM waveform, for example, prior to beginning the controlled breathing protocol. Such BPM waveform may be derived from a PPG signal as described earlier. The PPG signal may have been acquired such that at least during part of acquisition, a breathing protocol was executed by the subject under test. The power spectrum of the BPM waveform may further be checked in order to determine if a power peak exists around a predefined frequency. For example, if the breathing protocol comprises a breathing cycle of 0.1 Hz, then it may be expected by some embodiments of the invention that a peak around 0.1 Hz will be observed in the power spectrum of the BPM waveform.

According to some methods in accordance with embodiments of the invention, failure to locate a significant power peak in the power spectrum of the BPM waveform around the frequency dictated by the breathing protocol executed by the subject, may result in a decision that proper execution of the breathing protocol cannot be verified, in which case, the method may discard the test data, and/or provide a message to a participant in the test, e.g., a medical practitioner or the test subject, that the data cannot be verified, and possibly suggesting to retry the test. In some embodiments of the invention, a significant power peak may be located by comparing the power peak around the dictated frequency to a threshold minimum power peak.

According to some embodiments of the invention, if a power peak around the frequency dictated by the breathing protocol is detected in the power spectrum of the relevant BPM power spectrum, then a corresponding power peak in a power spectrum of the PPG signal may be searched for. If a significant power peak, around the frequency dictated by the breathing protocol, is identified in the power spectrum of the PPG, then provided a set of criteria applied to the two described peaks are met, it may be determined, by some embodiments of the invention, that an indicator such as, but not limited to an RMR may be computed, based on the PPG signal.

As described above, a set of criteria may be applied to the peaks located in the power spectrums of the PPG signal and the BPM waveform. According to some embodiments of the invention, such criteria may involve parameters such as, but not limited to, peak heights, peak widths, a frequency range containing the peaks, or a correlation parameter between location of the peaks on the frequency spectrum and the frequency dictated by the executed breathing protocol. In other embodiments of the invention, a criterion may be the distance, in terms of frequency between the peaks, for example, the peaks in the BPM and PPG power spectrum are expected to be no more than 0.02 Hz apart.

According to some embodiments of the invention, a significant power peak may be defined by the relation of the peak's height to the height of other peaks contained within a predefined frequency range. For example, a power peak around 0.1 Hz may be considered significant if it is at least three or four times higher than any other peak in the surrounding frequencies, for example, from 0.06 Hz to 0.12 Hz.

Figure 20B:
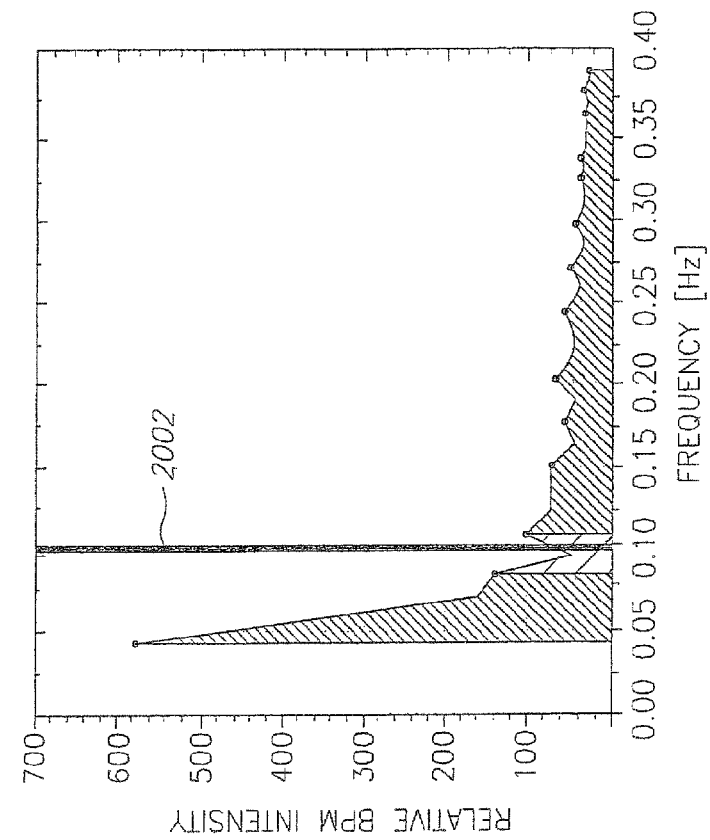
FIG. 20 shows an illustration of a power spectrum of a BPM acquired according to an embodiment of the present invention.
Figure 20A:
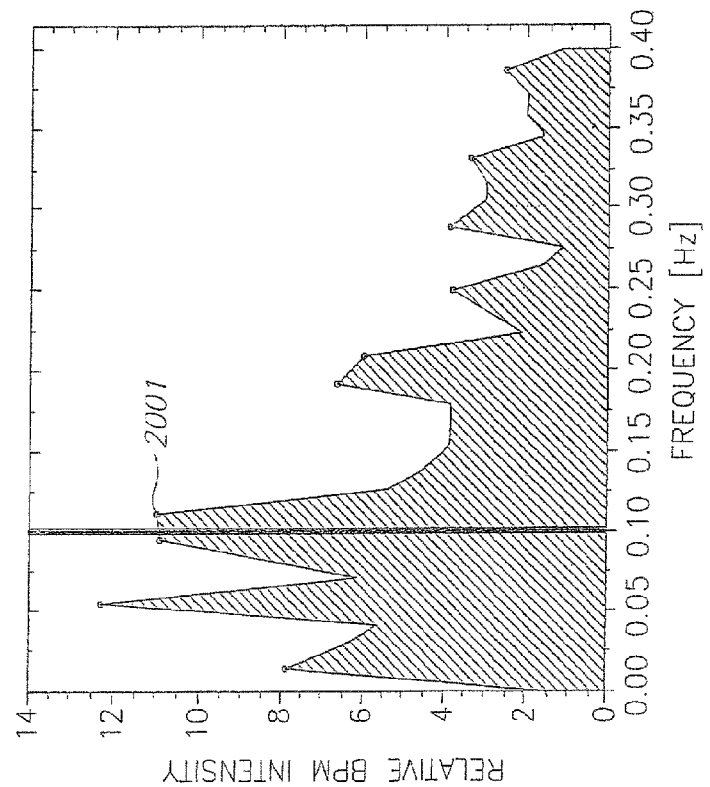

Reference is now made to FIG. 20A, which shows an exemplary power spectrum of a BPM waveform according to an embodiment of the present invention. According to some embodiments of the invention, the power peak around 0.1 Hz frequency, marked by the marking line 2001, may be considered significant. Consequently, it may be determined by some embodiments of the invention, whether a breathing protocol was executed correctly during acquisition of the corresponding PPG.

Reference is now made to FIG. 20B showing an exemplary power spectrum of a PPG signal. A marking line 2002 is placed on the 0.1 Hz frequency. According to some embodiments of the invention, the power spectrum shown in FIG. 20B has no significant power peak around 0.1 Hz. According to some embodiments of the invention, based on the power spectrum shown in FIG. 20B it may be determined that a RMR indicator may not be computed for the corresponding subject. In the example of FIG. 20B, it may be observed that there is no significant power peak at 0.1 Hz, and indeed a nadir exists around 0.1 Hz. Such a low or negative RMR indicator, e.g., below a predetermined threshold, may indicate a possible medical problem or condition, and a user may be advised accordingly.

According to some embodiments of the invention, a respiratory modulation response (RMR) indicator corresponding to a plurality of frequency ranges may be computed. For example, harmonics of a base frequency may be used, where harmonic frequencies may be integer multiples of a base frequency. For example, if the base frequency is 0.1 Hz then harmonic frequencies may be integer multiples thereof, e.g., 0.2 Hz, 0.3 Hz, etc. According to some embodiments of the invention, power peaks may be searched for around harmonic frequencies of a predetermined base frequency. Power peaks may be searched for and/or located, as described earlier. If such peaks are located, an RMR(i) indicator may be computed for each power peak located, where RMR(i) may denote the RMR computed for the i'th peak, where i may be the integers 1, 2, 3, etc.

According to some embodiments of the invention, a combined RMR indicator may be calculated as a function of an RMR(i) set. According to some embodiments of the invention, i may equal 0, and consequently, the calculated RMR may include the base frequency in the calculation. Example for functions that may be used for calculating a combined RMR as a function of the RMR(i) set may be an average of an RMR(i) set, a weighted average of an RMR(i) set, a weighed summation, a median, mode or a midrange of an RMR(i) set.

Figure 21:
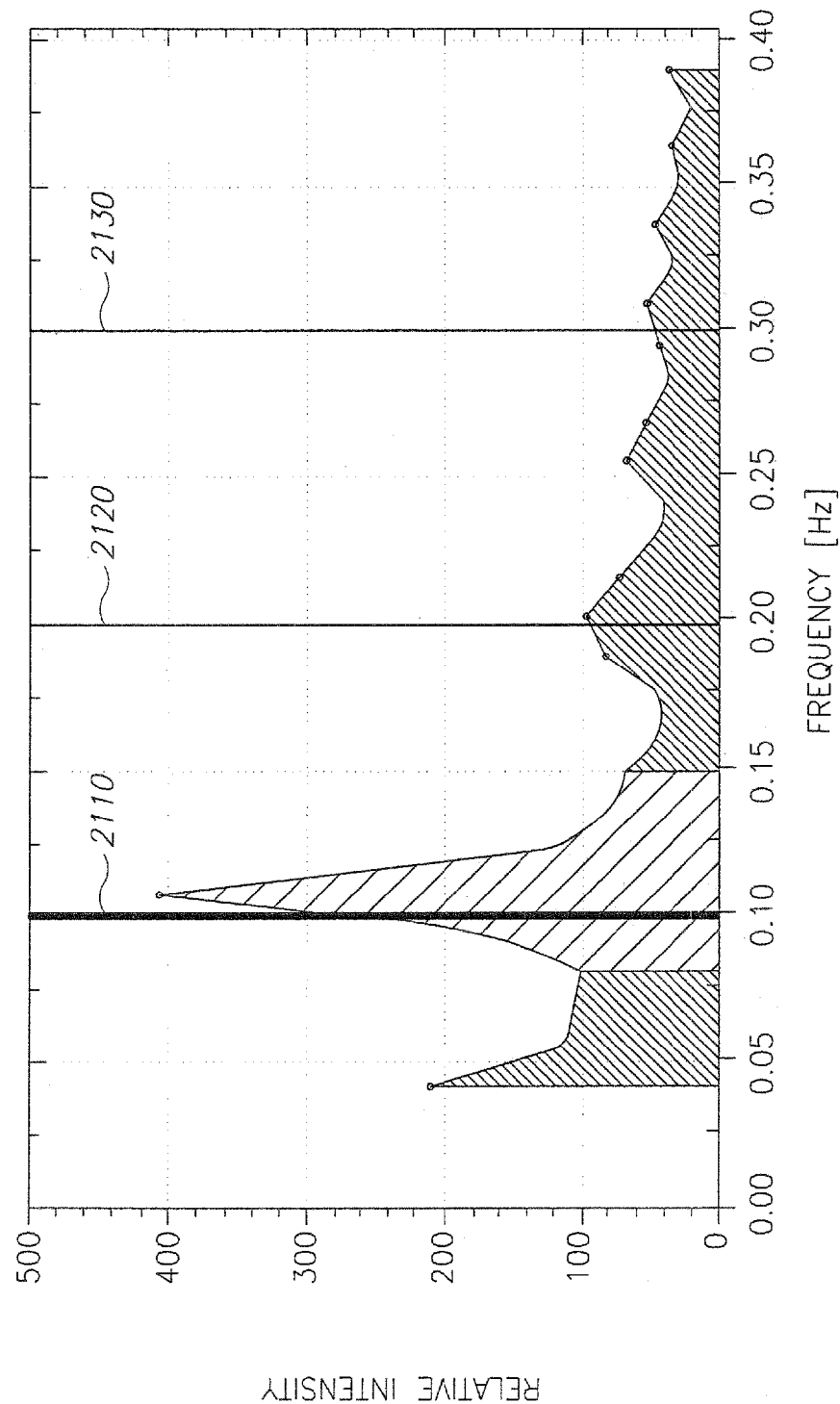
FIG. 21 shows an exemplary power spectrum of a PPG signal according to embodiments of the present invention.

Reference is now made to FIG. 21 showing an exemplary power spectrum of a PPG signal. marking lines are placed on a base frequency 0.1 Hz (2110) and two harmonic frequencies of 0.1 Hz, 0.2 Hz (2120) and 0.3 Hz (2130). According to some embodiments of the invention, the power peaks around the 0.2 Hz and 0.3 Hz may be considered significant. Consequently, a RMR(i), where i equals 0, 1 and 2 may be computed for each of the three peaks and the resulting RMR(i) set may be used, as described earlier, in order to compute the RMR indicator.

The above described computation can be performed using data extracted from the measured PW signal. For instance, an additional indicator (also termed herein 'PP RMR') may be computed using the pp series which was defined hereinabove.

Figure 22:
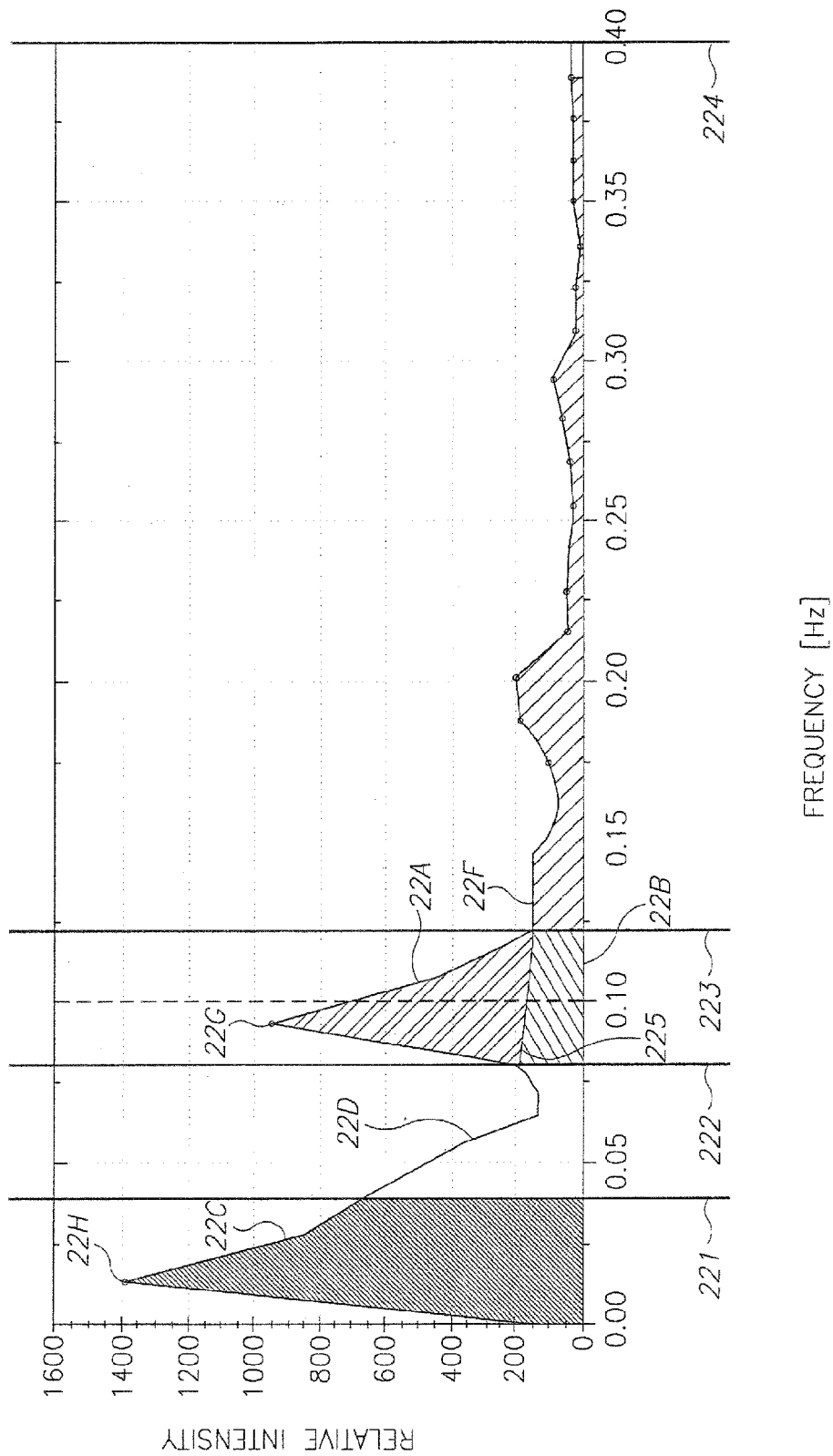
FIG. 22 shows an exemplary illustration of a power spectrum showing portions of an area usable for calculating RMR indicators according to embodiments of the invention.

Reference is now made to FIG. 22 showing an exemplary power spectrum that may be computed according to a PPG signal as described above. FIG. 22 further shows regions of the power spectrum that may be defined and further used for calculating RSR indicators according to embodiments of the invention. According to some embodiments of the invention, regions may be defined with respect to frequencies and/or frequency ranges. According to some embodiments of the invention, a power spectrum may be divided according to frequency ranges. For example, as shown by the markers 221, 222, 223, and 224 in FIG. 22, a number of frequency ranges may be defined. According to embodiments of the invention, a low frequency range may be defined, for example, marker 221 may define a frequency range containing frequencies from 0 Hz to a predefined frequency, e.g., 0.02 Hz or 0.04 Hz. According to some embodiments of the invention, a frequency range corresponding to a natural resonance frequency of a tested subject may be defined. Such frequency range may include the resonant frequency and frequencies within close proximity. For example, for a cardiovascular system with a resonant frequency of 0.1 Hz, a frequency range delimited by markers 222 and 223 may be defined such that the frequency of 0.1 Hz is included in such range. For example, marker 222 may correspond to a frequency of 0.08 Hz and marker 223 may correspond to a frequency of 0.12 Hz.

An exemplary division, such as shown in FIG. 22, may be such that the region denoted by 22D delimited by markers 221 and 222 may cover a range between a low frequency range and a resonant frequency range. For example, marker 222 may correspond to a frequency of 0.08 Hz. Accordingly, a frequency range of 0.04 Hz to 0.08 Hz may be defined by markers 221 and 222. According to embodiments of the invention, a frequency range above a range containing a resonant frequency may be defined. For example, markers 223 and 224 may define a frequency range above the resonant frequency range. For example, marker 223 may correspond with a frequency of 0.12 Hz and marker 224 may correspond with a frequency of 0.15 Hz. According to embodiments of the invention, regions may further be defined according to relative intensities, levels, values or other parameters pertaining to the power spectrum. For example, region 22A may further be limited to relative intensity values above a predefined minimum level, for example, as shown by 225. For example, such predefined minimum level may be an estimated base line and/or rest state level. Such estimated base line is shown in FIG. 22 as the line separating region 22A from region 22B.

Accordingly, the region denoted by 22B may correspond to or be delimited by the frequency range between markers 222 and 223. Region 22B may further be limited to relative intensity values below the estimated base line as shown. As shown, the region denoted by 22F may correspond to power spectrum levels delimited by a frequency range from marker 223 to marker 224. It will be recognized that according to embodiments of the invention, other divisions of the power spectrum may be applied and/or used. For example, marker 222 separating regions 22C and 22D may be moved up or down in the frequency range or the marker lines delimiting region 22A and 22B may be moved either up or down frequency wise. Such alterations may be performed without departing from the scope of the invention. Alternatively, the power spectrum level separating regions 22A and 22B may also be lifted or lowered or it may be other than a straight line.

According to embodiments of the invention, RSR indicators may be computed or derived by relating parameters associated with regions such as described above. For example, an RSR indicator may be computed by comparing an area of one or more regions to an area of one or more other regions. Alternatively, an RSR indicator may be computed by dividing a sum of areas of a first group of regions by a sum of areas of a second group of regions.

According to embodiments of the invention, any applicable parameters associated with regions such as those described above may be used. For example, such a parameter may be a perimeter of a region, one or more maximum or minimum values associated with a region or any other applicable parameters.

According to embodiments of the invention, the following exemplary calculations using an area parameter of regions shown in FIG. 22 may be used in order to compute RSR indicators. For example, a RSR indicator may be computed by dividing the area of regions covering the peak around the resonant frequency (e.g., 22A and 22B) by the sum of the areas of other, predefined regions (e.g., 22C, 22D and 22F) as follows:

$$RSR2 = \frac{22A + 22B}{22C + 22D + 22F}$$

Alternatively or additionally, a RSR indicator may be computed by dividing the area of a region covering a portion of the peak around the resonate frequency, for example, a region above a baseline marker (e.g., 22A) by a sum of areas of predefined regions, for example, regions covering areas other than the peak area and a region inside the peak area but further below a predefined baseline (e.g., 22B) as follows:

$$RSR3 = \frac{22A}{22B + 22C + 22D + 22F}$$

Other RSR indicators may be computed by dividing the area of a region covering the portion of the peak around the resonate frequency and further above a baseline marker (e.g., 22A) by a sum of the areas of regions surrounding and/or close to, the peak as follows:

$$RSR4 = \frac{22A}{22D + 22F}$$

or $$RSR5 = \frac{22A}{22F}$$

or $$RSR6 = \frac{22A}{22B}$$

or $$RSR7 = \frac{22A}{22D}$$

or $$RSR8 = \frac{22A}{22B + 22D + 22F}$$

Other RSR indicators may be computed by dividing the area of regions covering the peak around the resonate frequency (e.g., 22A and 22B) by a sum of the areas of regions surrounding the peak as follows:

$$RSR9 = \frac{22A + 22B}{22D + 22F}$$

According to embodiments of the invention, a RSR parameter may be computed by relating various aspects, values or parameters of a power spectrum as described above. For example, a RSR may be computed by relating specific values of the power spectrum shown in FIG. 22, e.g., the relative intensity at peak point 22G divided by the relative intensity at peak point 22H as follows:

$$RSR10 = \frac{22G}{22H}$$

The function of the ANS can be monitored according to the following indicators (step 34 in FIG. 3):

BPM Range—the difference between the maximal and minimal values of the BPM series. BPM Range values between 0 to 10 generally indicates ANS dysfunction, while values between 10 to 40 generally indicates normal functioning system.

pNN50—The percentage of PP intervals, differing by more then 50 mS, from subsequent PP interval. pNN50 values in the range 0% to 3% generally indicates ANS dysfunction, while values in the range 5% to 40% generally indicates normal functioning system.

Pulse Period Range—the range of variations of the PP series.

BPM STDEV—the standard deviation of the BPM series.

The following parasympathetic function indicators are extracted from the PW signal during excitation:

Responsive Pulse Rate Range (RPRR)—BPM series range during stimulation (e.g., controlled breath protocol). RPRR values in the range 0 to 10 generally indicates ANS dysfunction, while values in the range 11 to 40 generally indicates a normal functioning system.

Responsive Pulse Rate STDEV (RBPM-STDEV)—standard deviation of the BPM series obtained during the stimulation. RBPM-STDEV values in the range 0 to 2 generally indicates ANS dysfunction, while values in the range 3 to 10 generally indicates a normal functioning system.

Responsive pNN50 (RpNN50)—pNN50 during the stimulation. RpNN50 values in the range 0% to 5% generally indicates ANS dysfunction, while values in the range 6% to 80% generally indicates a normal functioning system.

Responsive Pulse Period Range (RPPR)—the range of variations of the PP series during stimulation. RPPR values in the range 0 to 30 generally indicates ANS dysfunction, while values in the range 50 to 100 generally indicates a indicates normal functioning system.

PP RMR—this indicator is the RMR computed from the power spectrum of the PP series.

The extracted scores (stiffness, flow, ANS, and total—steps 35-38 in FIG. 3) may be mapped to a range of values, for example, from 1 to 10, where 1 indicates good health and 10 worst illness situation.

The score calculation may be carried out as follows:

a. Mapping

The mapping is preferably a linear mapping using the following equation:

$$Val_{mapped} = k \cdot Val + (Range_{MIN} - k \cdot Val_{MIN})$$

Where:

$$k = \frac{Range_{MAX} - Range_{MIN}}{Val_{MAX} - Val_{MIN}}$$

$Range_{MAX}$—upper value of the mapping range (=10).

$Range_{MIN}$—lower value of the mapping range (=1).

$Val_{MAX}$—maximum possible value of the unmapped parameter.

$Val_{MIN}$—minimum possible value of the unmapped parameter.

$Val_{mapped}$—the parameter mapped in the new scale between $Range_{MIN}$ and $Range_{MAX}$.

b. Parameter Inversion

If the parameter value should be inverted (when larger values actually indicates a better condition, which should be properly inverted to a corresponding smaller value), the inversion is preferably done as follows.
$Val_{mapped} = Range_{MAX} - Val_{mapped}$.

c. The mapped score values are preferably remapped to a log scale, as follows—$Val_{mapped} = 10 \cdot \log_{10}(Val_{mapped})$.

d. The stiffness, flow and ANS, score values are calculated using the customized weighted coefficients Kparam, which are customized based on clinical results, as follows:

$$Val_{maped} = \frac{\sum_{i}^{N} K_{Param_i} \cdot Val_{mapped}^{Param_i}}{\sum_{i}^{N} K_{Param_i}}$$

The total score may be calculated utilizing the following customized weighted coefficients Kstifness, KANS and KFlow:

$$Val_{mapped}^{total} = \frac{K_{stifness} Val_{mapped}^{stiffness} + K_{ANS} Val_{mapped}^{ANS} + K_{Flow} \cdot Val_{mapped}^{Flow}}{K_{stifness} + K_{ANS} + K_{Flow}}$$

The following examples demonstrate some of the possible applications of the system of the invention, such as:

I. Cardiovascular risk screening and assessment.
II. cardiovascular intervention monitoring.
III. cardiovascular intervention follow-up.
IV. therapeutic strategy monitoring (including medications and life style changes such as diet and sports).

EXAMPLE 1

Figure 13A:
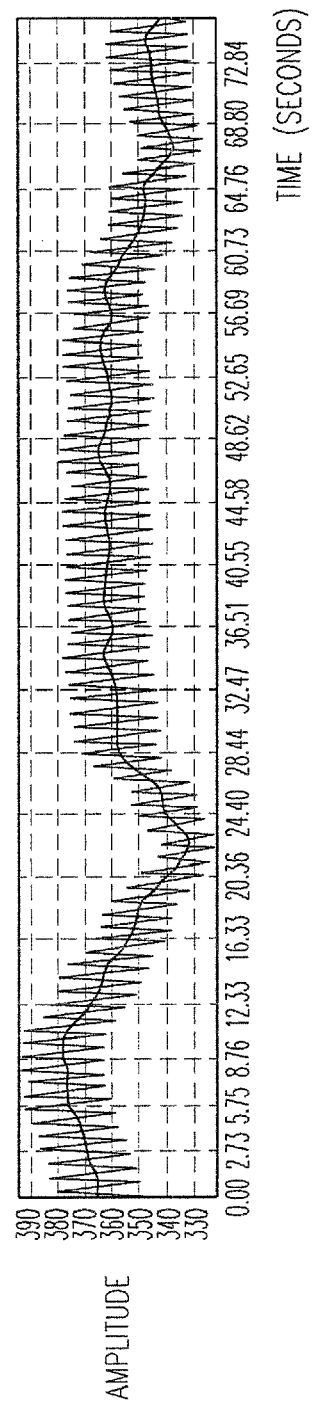
FIGS. 13A-C, 14A-C, 15A-C, and 16A-C, shows results of various tests according to the invention.
Figure 13B:
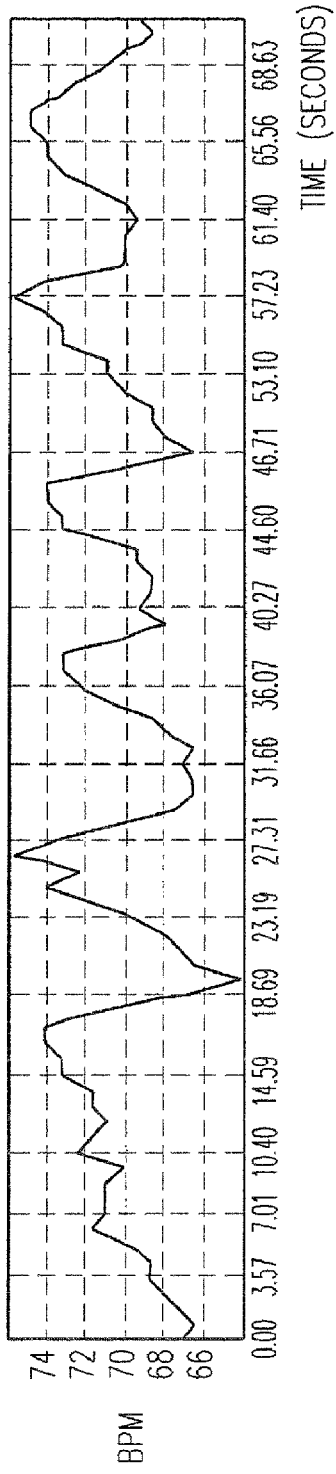
Figure 13C:
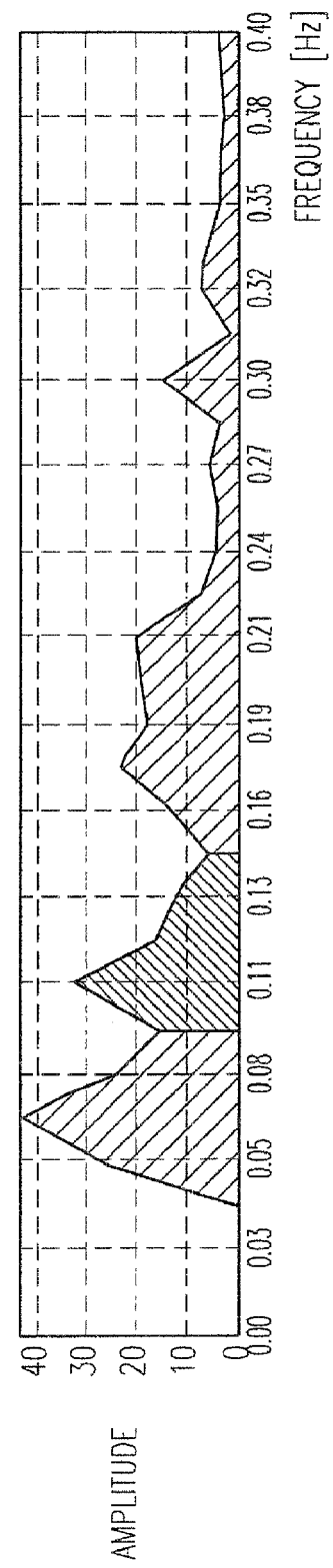

FIGS. 13A to 13C show the results of the test procedure of the invention performed with a patient. In this example the patient had a mild non-ST MI few weeks after having the test. The patient went through a PTCA procedure, which revealed a blocked artery, and underwent a stenting procedure. The PW signal measured during test shown in FIG. 13A shows that the relative amplitude (with respect to the breath-curve) of the PW signals remained almost unchanged during the test, which indicates that the blood system of this patient responded very weakly to the breath control stimulation. FIG. 13B, which show the HRV plot of the measured PW signal, confirms that the patient had a weak response to the excitation performed in the test. This weak response is also reflected in the spectrum of the PW signal depicted in FIG. 13C.

Table 1 lists the indicators calculated in this test and their diagnostic indication:

TABLE 1

| Indicator | Result | Indication |
|---|---|---|
| RPRR | 11 | Marginal |
| RPRV - STDEV | 2.6 | Marginal |
| RpNN50 | 0% | High risk |
| IR RMR | −15% | Very high risk |
| AI | 1.17 | Very high risk |
| Conclusions | | High risk for event |

Conclusions:
Flow indicators indicate a very high risk for an event.
All pulse rate variability indicators are marginal.

EXAMPLE 2

Figure 14A:
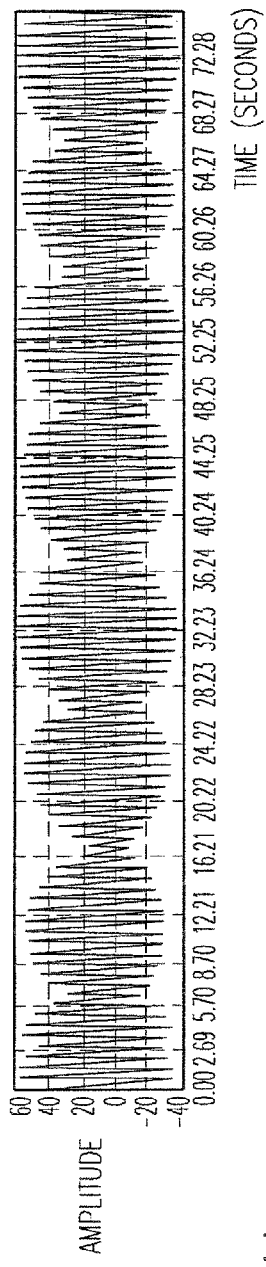
Figure 14B:
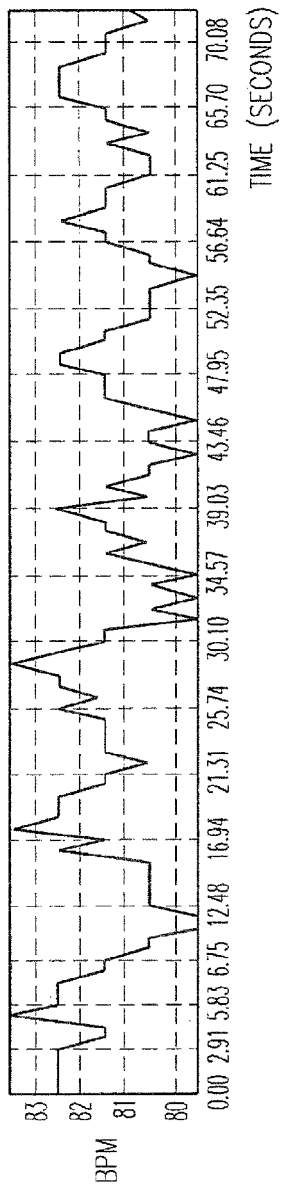
Figure 14C:
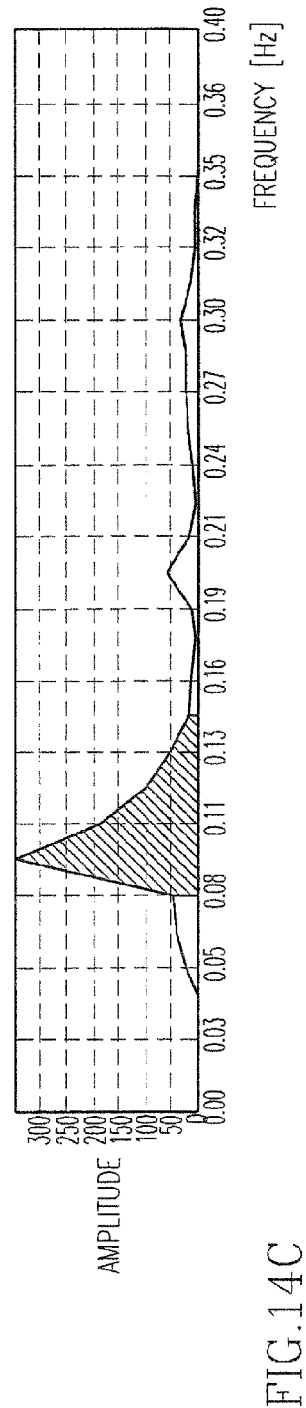

This example show the results of a test carried out with the same patient 1 day after the stenting procedure. As seen in FIGS. 14A and 14C, the amplitude and spectrum of the measured PW signal reveals significant improvement in the patient's response to the stimulation of the test, but the HRV plot shown in FIG. 14B indicates a relative reduction in the heart rate in response to the stimulation. The calculated indicators are listed in table 2 below.

TABLE 2

| Indicator | Result | Indication |
|---|---|---|
| RPRR | 4 | Very high risk |
| RPRV - STDEV | 1.0 | Very high risk |
| RpNN50 | 0% | Very high risk |

TABLE 2-continued

| Indicator | Result | Indication |
|---|---|---|
| IR RMR | 60% | Very good response |
| AI | 0.44 | Very good response |
| Conclusions | | Med-High risk for event |

Conclusions:
Flow indicators are very strong after stent procedures.
All Pulse rate variability indicators are very low (the MI probably damaged the patient's autonomic nervous system).

EXAMPLE 3

Figure 15A:
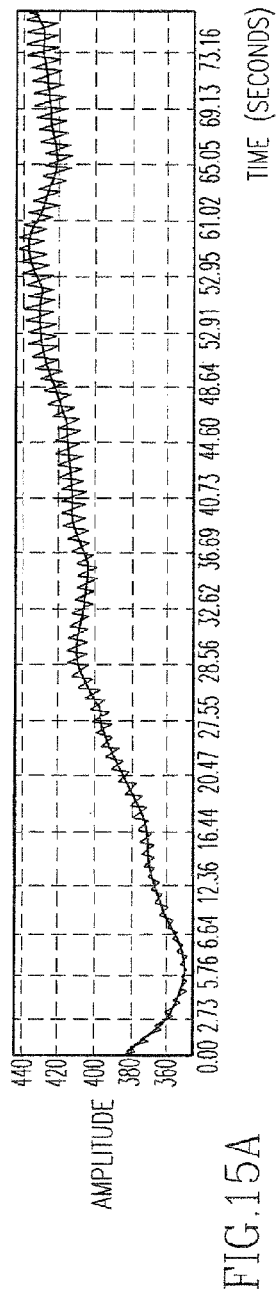
Figure 15B:
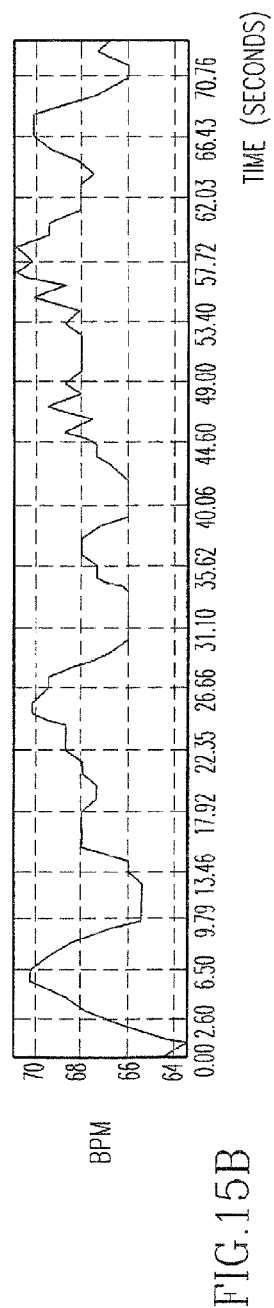
Figure 15C:
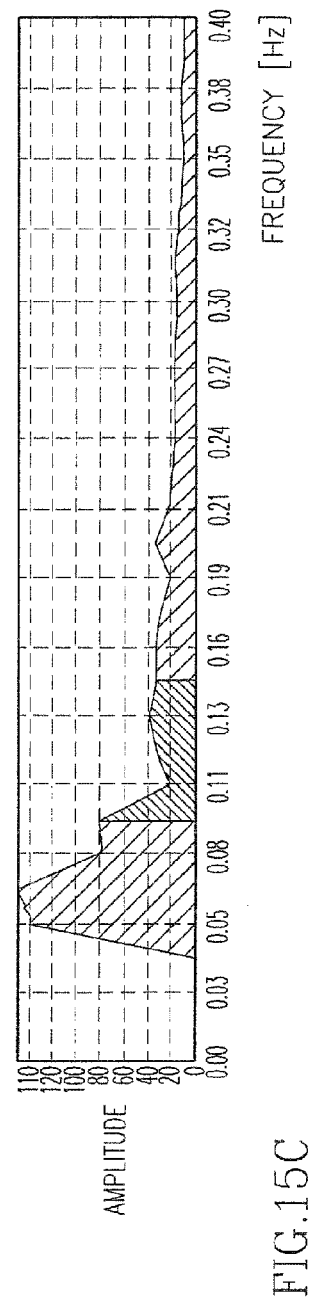

This example show the results of a test carried out with the same patient 30 days after the event. During this time the patient received anti cholesterol medication (with a statin drug), and reported that he felt very ill. As seen in FIGS. 15A-15C, the PW response is very weak, indicating a possible restenosis.

Table 3 lists the indicator calculated in this test and their diagnostic indication:

TABLE 3

| Indicator | Result | Indication |
|---|---|---|
| RPRR | 4 | Very high risk |
| RPRV - STDEV | 1.6 | Very high risk |
| RpNN50 | 0% | Very high risk |
| IR RMR | −10% | Very high risk |
| AI | 1.35 | high risk |
| Conclusion | | Very high risk |

Conclusions:
Flow indicators have been regressing - possible restenosis.
All pulse rate variability indicators are still very low.

EXAMPLE 4

This example show the results of a test carried out with the same patient after changing medications, changed diet, and increased physical activity.

Table 4 lists the indicator calculated in this test and their diagnostic indication:

TABLE 4

| Indicator | Result | Indication |
|---|---|---|
| RPRR | 10 | Marginal |
| RPRV - STDEV | 1.6 | high risk |
| RpNN50 | 2.3% | high risk |
| IR RMR | 40% | low risk |
| AI | 1.11 | med risk |
| Conclusion | | Marginal |

Figure 16A:
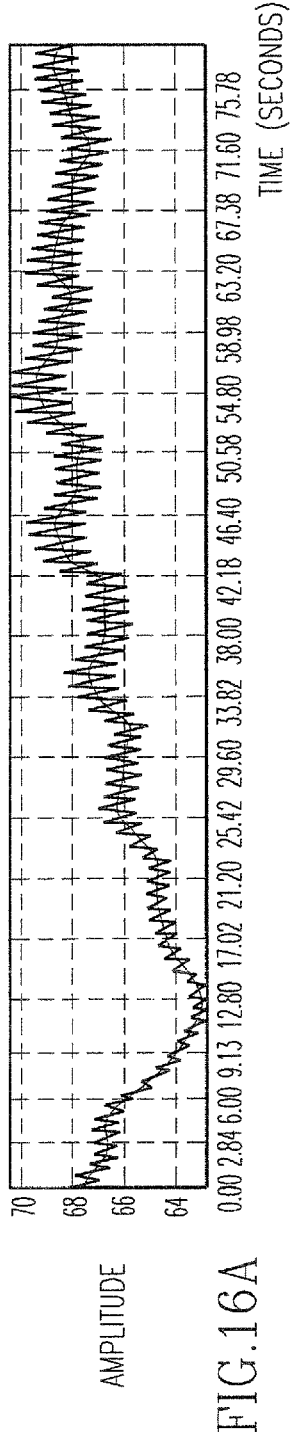
Figure 16B:
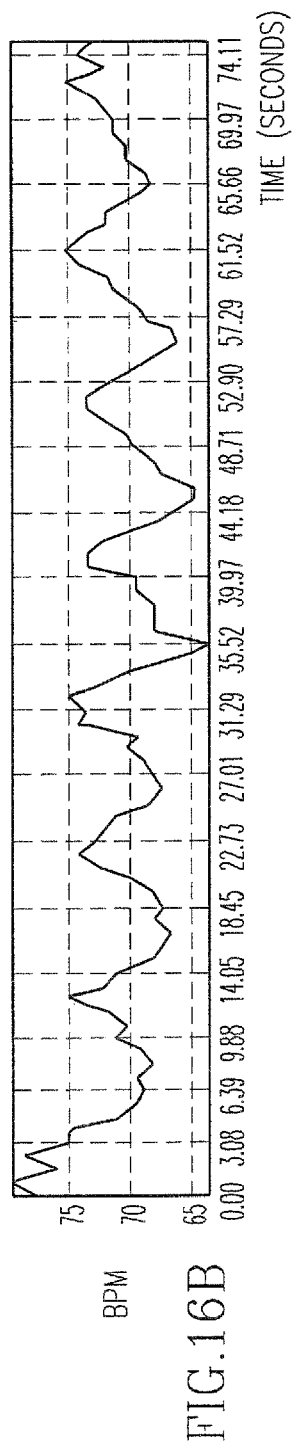
Figure 16C:
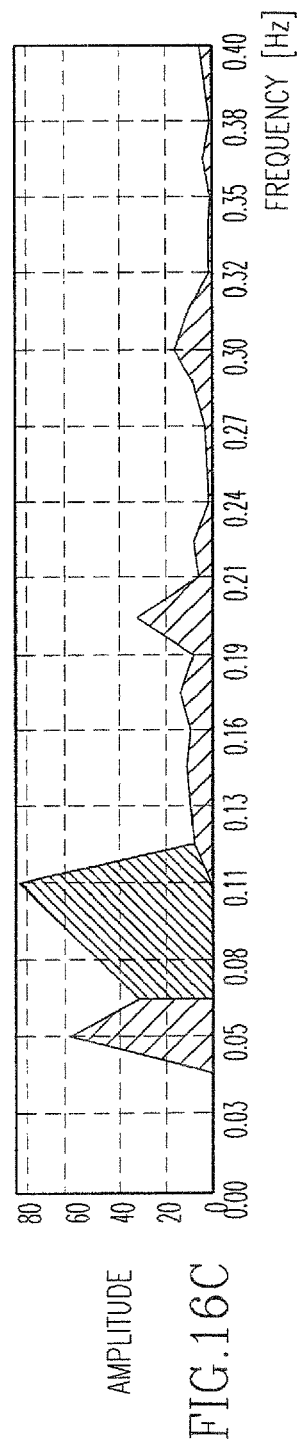

As seen in FIGS. 16A-16C the conclusions:
Flow indicators have recovered.
Pulse rate variability indicators are improving due to diet and exercise.

EXAMPLE 5

Figure 17A:
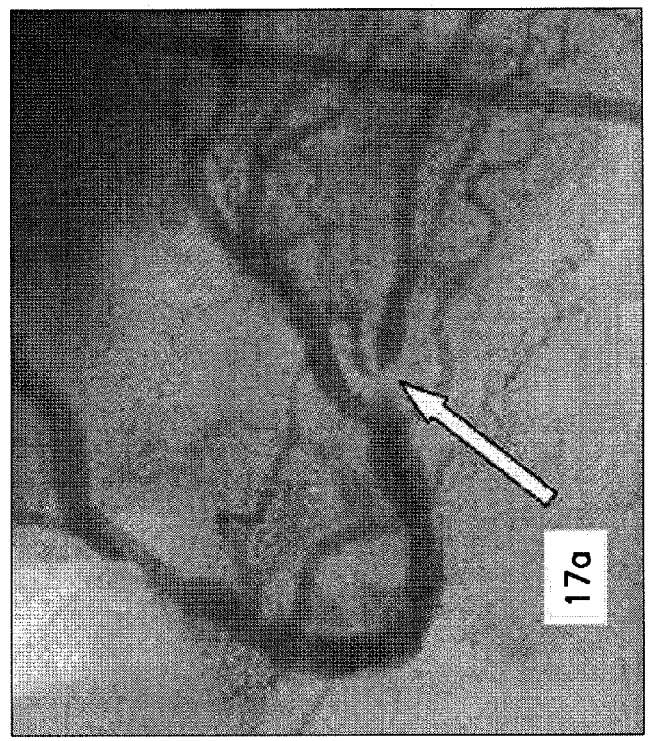
FIGS. 17A, 17B, and 17C, respectively shows an X-ray image of coronary blood vessels, pulse wave signal, and the power spectrum of the pulse wave signal, of a patient suffering from a coronary artery occlusion.
Figure 17B:
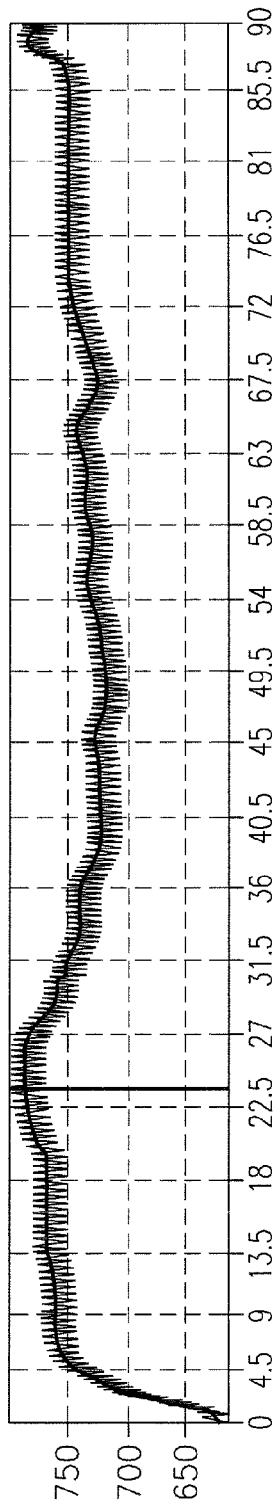
Figure 17C:
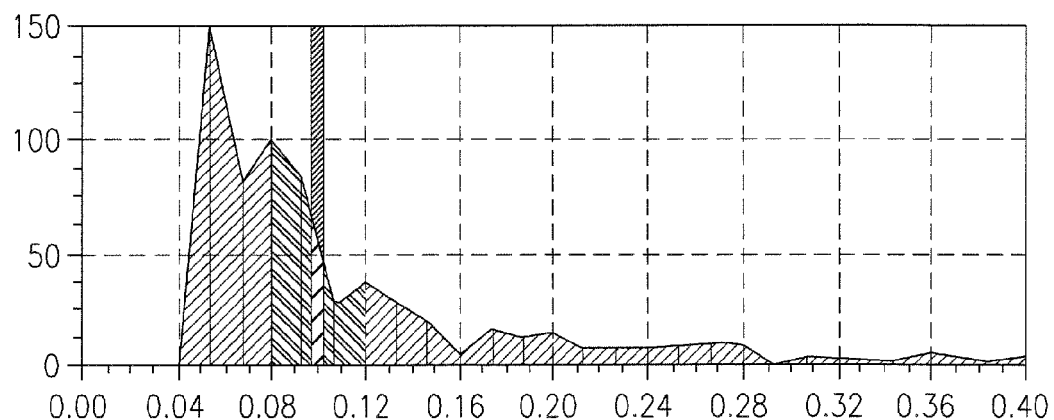

FIGS. 17A, 17B, and 17C, respectively shows an X-ray image of coronary blood vessels, pulse wave signal, and the power spectrum of the pulse wave signal, of a patient suffering from a coronary artery occlusion. As shown in FIG. 17A, a coronary blood vessel 17a of the patient is blocked, the PW signal (FIG. 17B) measured during the test process shows a decrease in the vascular system function in response to the excitation, and the frequency domain transformation of the PW signal shown in FIG. 17C indicates a low RMR.

Figure 18A:
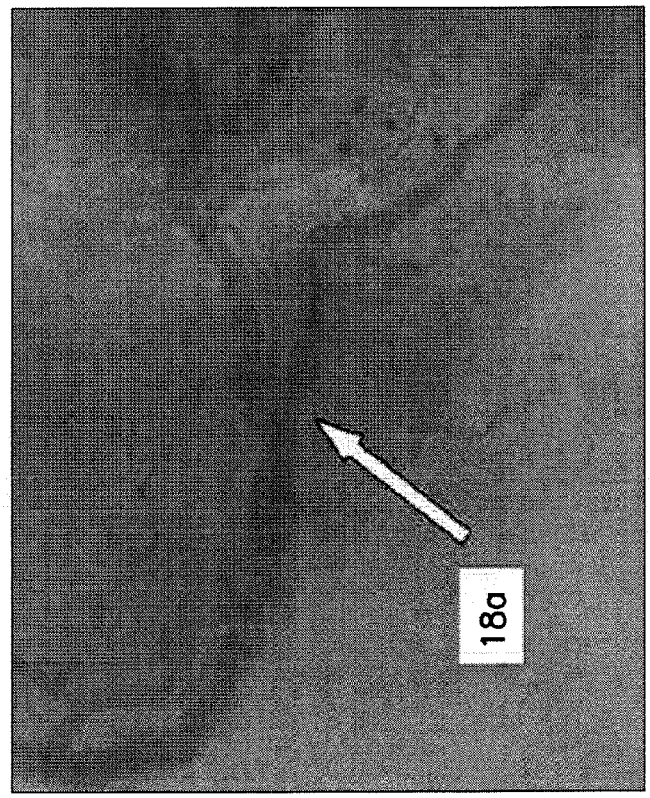
FIGS. 18A, 18B, and 18C, respectively shows an X-ray image of coronary blood vessels, pulse wave signal, and the power spectrum of the pulse wave signal, of the same patient of FIGS. 17A-17C, after a stenting procedure.
Figure 18B:
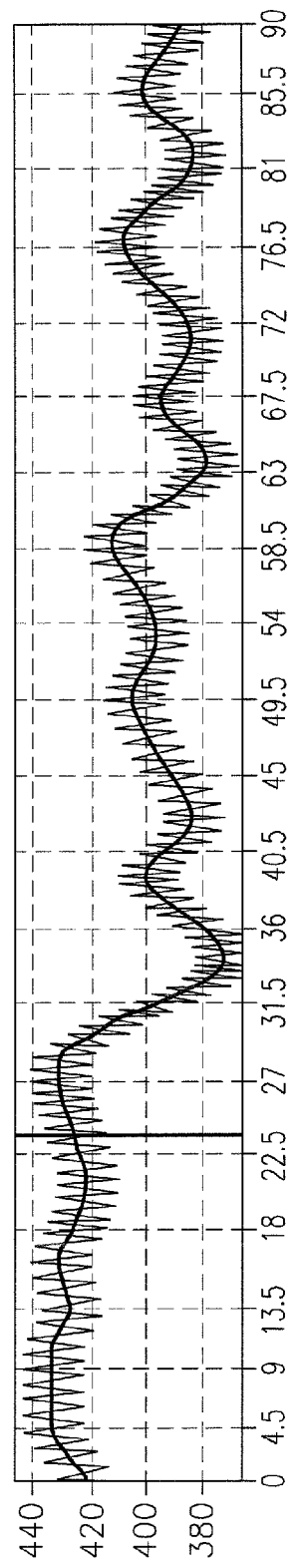
Figure 18C:
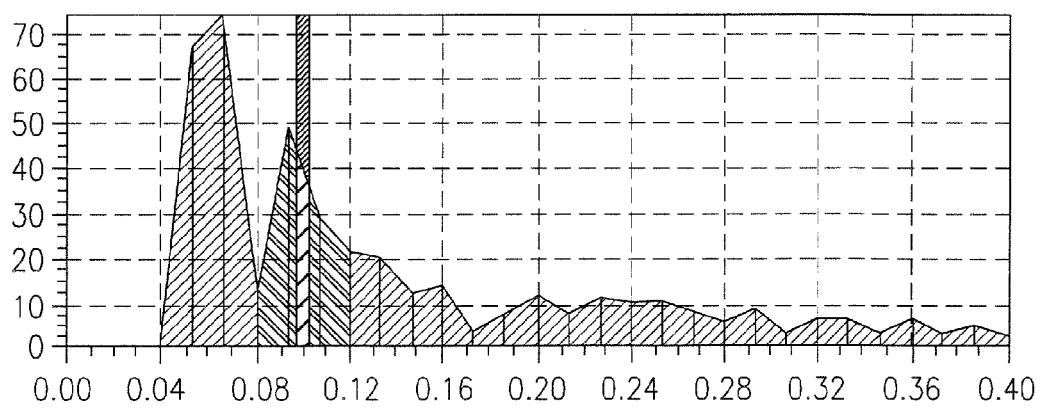

FIGS. 18A, 18B, and 18C, respectively shows an X-ray image of coronary blood vessels, pulse wave signal, and the power spectrum of the pulse wave signal, of the same patient of FIGS. 17A-17C, after a stenting procedure. As shown in FIG. 18A the blood vessel blockage 18a was opened by the stent, the PW signal measured during the test shown in FIG. 18B indicates an improvement in the cardiovascular response to the excitation, and the power spectrum shown in FIG. 18C also shows RMR improvement.

The system of the present invention was tested with 20 patients (mean age 63±11 years, 13 male). The results obtain for 10 of the tested patients were compared with coronary angiography results, and the results obtained for the remaining 10 patients were compared with SPECT Thallium myocardial perfusion scan (TL—a test in which thallium is injected into the patient's blood system for diagnosing the blood flow to the heart muscle). The tested patients performed the controlled breathing protocol, which was previously described hereinabove, consisting of 20 second spontaneous breathing (baseline), followed by 70 seconds of guided deep breathing.

Figure 3:
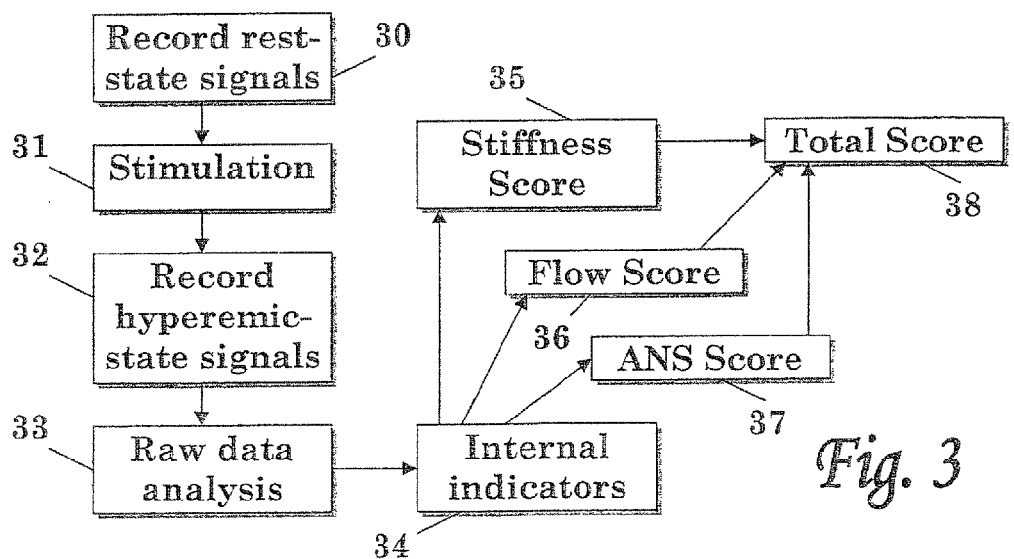
FIG. 3 is a flowchart illustrating the test and analysis process according to a preferred embodiment of the invention.

In the results obtained the average arterial flow score index, described in p. 16, and item 36 in FIG. 3 (normal ranges 1 [best] to 10 [worst]) was lower in 3 patients shown to have moderate to severe ischemia in at least one segment compared with 6 patients shown to have no ischemia in the TL SPECT test (7.7.±0.6 vs. 3.5±1.2). In one of the patients with minimal reversible ischemia, the arterial flow score index was 5. Coronary angiographies demonstrated severe CAD in 6 patients. In 5 patients the average flow score index was −8.3±1.4 (6 to 10). In the $6^{th}$ patient (with a score of −4), collaterals were the likely explanation. In 2 patients with non-significant CAD the arterial flow score was low: 3±0. Post PCI (Percutaneous coronary intervention) in 5 patients, the result of average flow score improved from 8.0±1.6 to 3±2.5. These results shows that test scheme of the invention during deep breathing has potential for use as a screening tool for CAD.

Further Results for the RMR Indicator

Methods: The RMR results of 124 consecutive patients; (mean age 62.8±11.7 years, 81% male) referred for coronary angiography were compared with their coronary angiography results. Patients undergoing PCI or CABG (coronary artery bypass graft) were classified as having significant CAD. The test was performed by a single operator in the recovery room of the catheterization laboratory prior to the procedure. RMR was analyzed after baseline 20 seconds spontaneous breathing, followed by 70 seconds of guided deep breathing at 0.1 Hz. The test was repeated post procedure in 93 patients following PCI or diagnostic catheterization.

Results: The RMR (normal ranges 72% [best] to 0% [worst]) was significantly lower in patients with significant CAD (n=85) vs. patients with non-significant CAD (n=39) (17.96±20.18 vs. 39.49±16.16, P<0.001). The improvement in post procedure RMR was significantly higher in patients undergoing successful PCI as compared to patients undergoing diagnostic catheterization only (24.86±23.70 vs. −0.26±18.04, P<0.001). RMR was lowest at the subgroup of patients with recent MI (0.33±0.71 vs. 26.74±21.17, P<0.001). By using a receiver operating characteristic analysis, an RMR<30% (sensitivity 0.75, specificity 0.85) was identified to be the optimal cutoff value for predicting significant CAD, Results were superior with the subgroup of non-diabetics: (sensitivity 0.83, specificity 0.94).

Conclusions: The novel digital PWA analysis test during deep breathing using the system of the present invention is a simple, non-invasive bedside or office based test to detect significant CAD and to follow patients with CAD post PCI.

Further Results for Other Indicators

The following indicators were tested on 124 heart patients, and compared to 280 healthy subjects:

|  | AI | PNN50 % | SD BPM | Range BPM |
| --- | --- | --- | --- | --- |
| Healthy AVG | 0.81 | 28.26 | 7.69 | 31.02 |
| Healthy STDEV | 0.29 | 21.2 | 4.77 | 19.25 |
| CVD* patients | 1.035 | 8.60 | 2.76 | 12.94 |
| CVD STDEV | 0.22 | 15.157 | 2.517 | 10.04 |
| P value** between groups | <0.05 | <0.001 | <0.001 | <0.001 |

*CVD—Cardio Vascular Disease.
**P value - Statistical significance.

As previously mentioned, although a PPG sensor is utilized to exemplify the preferred embodiment of the invention, the invention can be carried out utilizing other types of sensors. For example, similar results can be obtained by utilizing a pressure blood sensor. While some changes may be required, these changes can be easily carried out by those skilled in the art. In addition, while in the above examples the PW signal is obtained from the finger of tested subject, it should be clear that the PW signal can be measured in any other part of the body, such as the ear, neck, wrist, ankle, toe, chest, or even invasively.

Additional indicators for cardiovascular function assessment that have not yet been developed to date may be utilized with the present invention. While various embodiments of the present invention have been described in detail, it is apparent that further modifications and adaptations of the invention will occur to those skilled in the art. However, it is to be expressly understood that such modifications and adaptations are within the spirit and scope of the present invention.

Some of the possible indicators that may be used in this invention are listed in table 5.

TABLE 5 additional possible indicators

| Name | Indication | Conventional analysis | Proposed analysis |
| --- | --- | --- | --- |
| Baro-reflex sensitivity | CVD event | Blood pressure monitoring | PPG at 0.1 Hz Breathing |
| Immediate Entrainment | CVD RISK | None | PPG time domain |
| Heart Rhythm Coherence | CVD event | ECG/PPG | Pattern Analysis |
| Perfusion Recovery Amplitude | Atherosclerosis, Endothelial dysfunction | Mechanical plethysmograph | Reactive hyperemia analysis |
| Perfusion Recovery Constant | Atherosclerosis, Endothelial dysfunction | none | Reactive hyperemia analysis |

As was described hereinabove in detail, the present invention provides indications for various physiological parameters, including, but not limited to:

Arterial stiffness (e.g., AI);
Arterial flow (e.g., HRV); and
Autonomic Nervous System control of cardiovascular activity (e.g., HRV Range).

These parameters are combined to form a single risk factor.

The present invention can be employed for various uses, such as, but not limited to:

Screening of the general population for identifying people at risk of cardiovascular events;
Monitoring the effect of medications;
Monitoring the effect of cardiovascular intervention;
Monitoring the effect of life style changes, such as dieting and exercising;

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

What is claimed is:

1. A method comprising:
   measuring, by a sensing device, blood pulse wave signals of a subject during a periodic excitation of a cardiovascular system of the subject, wherein the periodic excitation is at an excitation frequency around 0.1 Hertz;
   transforming, by a computational device, the blood pulse wave signals to a frequency domain representation by computing a power spectrum of the blood pulse wave signals;
   extracting, by a computational device, a respiratory stress response (RSR) indicator associated with a respiratory peak of the frequency domain representation around the excitation frequency; and
   evaluating the condition of the cardiovascular system of the subject based on the RSR indicator.

2. The method of claim 1, wherein the periodic excitation of the cardiovascular system is achieved by periodically applying pressure to an eyeball of the subject associated with the cardiovascular system.

3. The method of claim 1, wherein the periodic excitation of the cardiovascular system is achieved by periodically contracting extraocular muscles of the subject associated with the cardiovascular system.

4. The method of claim 1, wherein the periodic excitation of the cardiovascular system is achieved by periodically performing a Valsalva manoeuvre.

5. The method of claim 1, wherein the periodic excitation of the cardiovascular system is achieved by periodically performing a Muller manoeuvre.

6. The method of claim 1, wherein the periodic excitation of the cardiovascular system is breathing at the excitation frequency.

7. The method of claim 1, wherein the blood pulse wave signals are measured by a photoplethysmograph (PPG) sensor placed on a finger of the subject.

8. The method of claim 1, wherein the blood pulse wave signals are received from measurement of blood flow, blood volume or blood pressure of the subject.

9. The method of claim 1, wherein extracting the respiratory stress response (RSR) indicator comprises:
   defining a first frequency range in the frequency domain representation around the excitation frequency, the first frequency range is delimited by a low boundary frequency below the excitation frequency and a high boundary frequency above the excitation; and computing a first area parameter corresponding to an area delimited by a curve of the frequency domain representation within the first frequency range and a line connecting points on the curve that correspond to the low and high boundary frequencies, respectively.

10. The method of claim 9, wherein the low and high boundary frequencies are determined at points where the slope of the curve is smaller than a predefined value.

11. The method of claim 9, wherein extracting the respiratory stress response (RSR) indicator further comprises:
    computing a second area parameter that corresponds to an entire area under the curve of the frequency domain representation within the first frequency range; and
    computing the RSR indicator as the ratio between the first area parameter and the second area parameter.

12. The method of claim 9, wherein extracting the respiratory stress response (RSR) indicator further comprises:
    defining a second frequency range in the frequency domain representation between zero and a cut-off frequency, wherein the cut-off frequency is higher than the a high boundary frequency of the first frequency range;
    computing a third area parameter that corresponds to the entire area under the curve of the frequency domain representation within the second frequency range excluding the area associated with the first area parameter; and
    computing the RSR indicator as the ratio between the first area parameter and the third area parameter.

13. The method of claim 12, wherein the cut-off frequency is at around 0.4 Hertz.

* * * * *